(12) United States Patent
Botti et al.

(10) Patent No.: US 7,884,182 B2
(45) Date of Patent: Feb. 8, 2011

(54) CHEMICAL PEPTIDE LIGATION WITH THREE OR MORE COMPONENTS

(75) Inventors: Paolo Botti, Meyrin (CH); Hubert Gaertner, Geneva (CH); Sonia Manganiello, Geneva (CH); Matteo Villain, Meyrin (CH)

(73) Assignee: Amylin Pharmaceuticals, Inc., San Diego, CA (US)

( * ) Notice: Subject to any disclaimer, the term of this patent is extended or adjusted under 35 U.S.C. 154(b) by 636 days.

(21) Appl. No.: 10/494,928

(22) PCT Filed: Nov. 14, 2002

(86) PCT No.: PCT/IB02/05094

§ 371 (c)(1),
(2), (4) Date: Oct. 18, 2004

(87) PCT Pub. No.: WO03/042235

PCT Pub. Date: May 22, 2003

(65) Prior Publication Data

US 2005/0113563 A1 May 26, 2005

Related U.S. Application Data

(60) Provisional application No. 60/336,459, filed on Nov. 14, 2001, provisional application No. 60/334,268, filed on Nov. 29, 2001, provisional application No. 60/353,823, filed on Jan. 31, 2002.

(51) Int. Cl.
*A61K 38/00* (2006.01)
(52) U.S. Cl. .................................................. 530/324
(58) Field of Classification Search ............... None
See application file for complete search history.

(56) References Cited

U.S. PATENT DOCUMENTS 5,801,148 A  9/1998  Gyorkos et al.

2005/0113563 A1 * 5/2005 Botti et al. ............... 530/350

FOREIGN PATENT DOCUMENTS

WO  WO 00/18789 A  4/2000

OTHER PUBLICATIONS

Villain et al Chemical Ligation of Multiple Peptide Fragments Using a New Protection Strategy, Peptides: Wave of the Future (2001), p. 107.*
Botti, P. et al., "Native chemical ligation using removable N1pha-(1-phenyl-2-mercaptoethyl) auxiliaries," Tetrahedron Letters, vol. 42, No. 10; pp. 1831-1833 (Mar. 4, 2001).
Canne, L.E. et al., "Extending the applicability of native chemical ligation," J. Am. Chem. Soc., vol. 118, No. 25; pp. 5891-5896 (Jun. 26, 1996).
Freidinger, R. M., "Computer graphics and chemical synthesis in the study of conformation of biologically active peptides," Pept.: Synth., Struct, Funct., Proc. Am. Pept. Symp., 7th (1981) pp. 673-683 (eds.: Rich, D.H. and E. Gross).
Villain, M. et al., "Chemical ligation of multiple peptide fragments using a new protection strategy," in: Peptides: The Wave of the Future, Proceedings of the 2nd Int'l and 17th American Peptide Symposium, San Diego, CA, USA (Jun. 9-14, 2001) pp. 107-108 (eds. Lebl, M. and R.A. Houghten).

* cited by examiner

*Primary Examiner*—Cecilia Tsang
*Assistant Examiner*—Thomas S Heard
(74) *Attorney, Agent, or Firm*—Townsend and Townsend and Crew LLP

(57) ABSTRACT

The invention provides a method of assembling oligopeptide intermediates in a native chemical ligation reaction that eliminates self-ligation of bi-functional intermediates. An important aspect of the invention is a bi-functional intermediate with an N-terminal heterocyclic protecting group which effectively prevents self-ligation in the chemical assembly process. The present invention is useful in methods for convergent synthesis of polypeptides and proteins and improves the efficiency of native chemical ligation reactions, particularly where three or more peptide fragments are used to assemble a polypeptide or protein product.

7 Claims, 16 Drawing Sheets

Scheme 1

Scheme 2

Deprotect/Cleave (506)

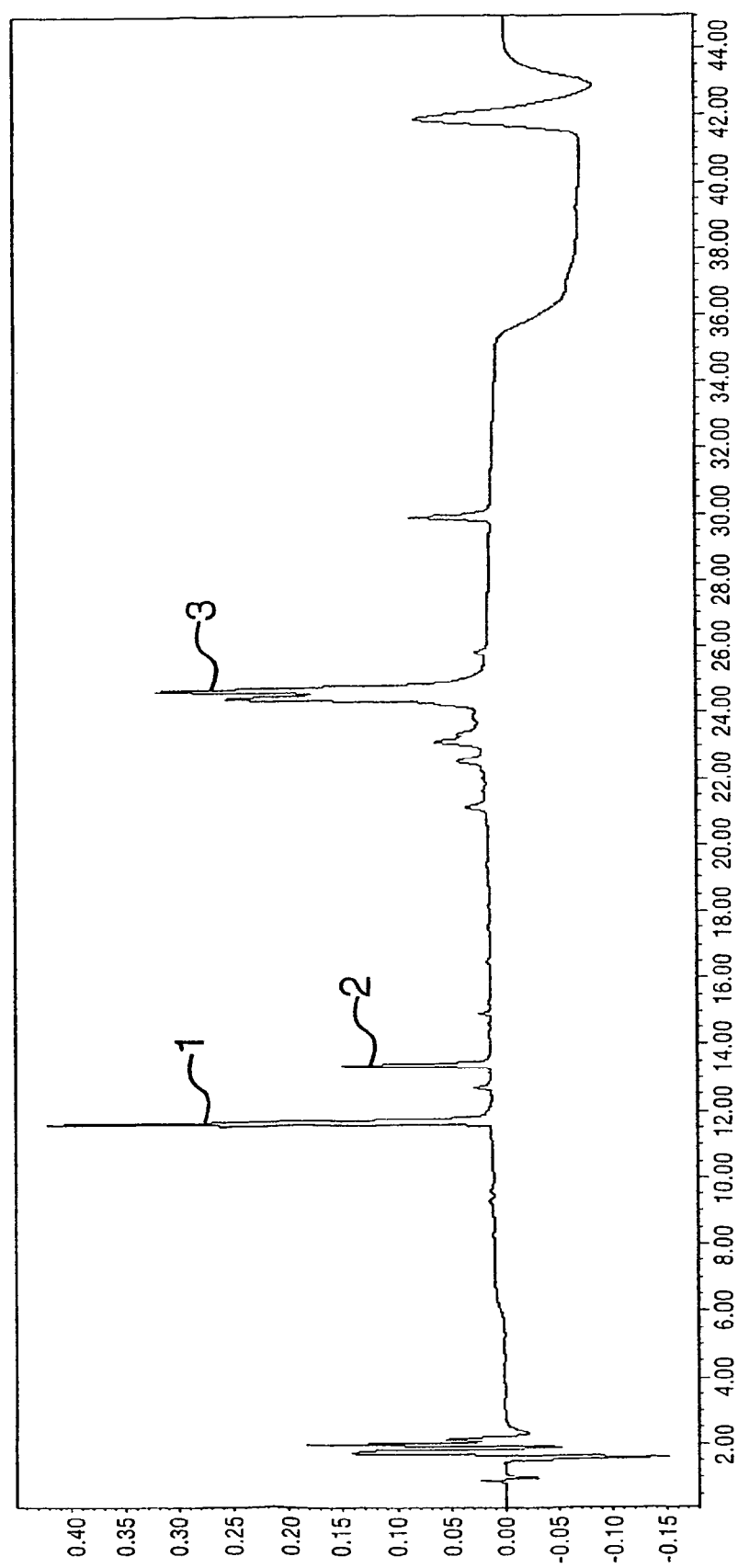

```
                        SEQUENCE LISTING

<160> NUMBER OF SEQ ID NOS: 7

<210> SEQ ID NO 1
    <211> LENGTH: 8
    <212> TYPE: PRT
    <213> ORGANISM: Artificial Sequence
    <220> FEATURE:
    <223> OTHER INFORMATION: Description of Artificial Sequence:synthetic
          oligopeptide (fragment 1) reactant having
          N-terminal cysteine, artificial model peptide

<400> SEQUENCE: 1

Cys Tyr Ala Lys Tyr Ala Lys Leu
      1               5

<210> SEQ ID NO 2
    <211> LENGTH: 32
    <212> TYPE: PRT
    <213> ORGANISM: Artificial Sequence
    <220> FEATURE:
    <223> OTHER INFORMATION: Description of Artificial Sequence:synthetic
          N-terminal 4-substituted 1,3-thiazolidine-protected
          oligopeptide thioester, artificial model peptide

<400> SEQUENCE: 2

Gly Ala Val Val Phe Val Thr Arg Lys Asn Arg Gln Val Ser Ala Asn
      1               5                  10                  15

Pro Glu Lys Lys Ala Val Arg Glu Tyr Ile Asn Ser Leu Glu Leu Leu
                 20                  25                  30

<210> SEQ ID NO 3
    <211> LENGTH: 31
    <212> TYPE: PRT
    <213> ORGANISM: Artificial Sequence
    <220> FEATURE:
    <223> OTHER INFORMATION: Description of Artificial Sequence:synthetic
          bromoacetylated oligopeptide thioester, artificial
          model peptide

<400> SEQUENCE: 3

Ala Val Val Phe Val Thr Arg Lys Asn Arg Gln Val Ser Ala Asn Pro
      1               5                  10                  15

Glu Lys Lys Ala Val Arg Glu Tyr Ile Asn Ser Leu Glu Leu Leu
                 20                  25                  30

<210> SEQ ID NO 4
    <211> LENGTH: 9
    <212> TYPE: PRT
    <213> ORGANISM: Artificial Sequence
    <220> FEATURE:
    <223> OTHER INFORMATION: Description of Artificial Sequence:N-terminal
          modified amino acid peptide fragment [N-terminalAA
          (Aux)-Peptide], artificial model peptide
    <220> FEATURE:
    <221> NAME/KEY: MOD_RES
    <222> LOCATION: (1)
    <223> OTHER INFORMATION: Xaa = alpha-N-(1-(4-methoxyphenyl)-2-
          mercaptoethyl Gly
```

```
<400> SEQUENCE: 4

Xaa Tyr Ala Lys Tyr Ala Lys Ala Leu
 1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence:amino acid
      sequence orders amino acids from the N-terminus to
      the C-terminus

<400> SEQUENCE: 5

Asp Lys Leu Leu Met
 1               5

<210> SEQ ID NO 6
<211> LENGTH: 32
<212> TYPE: PRT
<213> ORGANISM: Artificial Sequence
<220> FEATURE:
<223> OTHER INFORMATION: Description of Artificial
      Sequence:resin-boundoligopeptide thioester with
      trityl-protected sulfhydryl of auxiliary group
<220> FEATURE:
<221> NAME/KEY: MOD_RES
<222> LOCATION: (1)
<223> OTHER INFORMATION: Xaa =
      alpha-N-(1-(4-methoxyphenyl)-2-(tritylthio)-ethyl-
      Gly
<220> FEATURE:
<221> NAME/KEY: MOD_RES
<222> LOCATION: (32)
<223> OTHER INFORMATION: Xaa = Leu coupled to resin by -(CO)-S-
      (thioester) group

<400> SEQUENCE: 6

Xaa Ala Val Val Phe Val Thr Arg Lys Asn Arg Gln Val Ser Ala Asn
 1               5                  10                  15

Pro Glu Lys Lys Ala Val Arg Glu Tyr Ile Asn Ser Leu Glu Leu Xaa
            20                  25                  30

<210> SEQ ID NO 7
<211> LENGTH: 32
<212> TYPE: PRT
<213> ORGANISM: Artificial Sequence
<220> FEATURE:
<223> OTHER INFORMATION: Description of Artificial
      Sequence:alpha-N-(1-methyl-5-methoxyphenyl-
      1,3-thiazolidine)-protected oligopeptide thioester
      (fragment 2) synthetic oligopeptide reactant,
      artificial model peptide
<220> FEATURE:
<221> NAME/KEY: MOD_RES
<222> LOCATION: (1)
<223> OTHER INFORMATION: Xaa =
      alpha-N-(1-methyl-5-methoxyphenyl-1,3-thiazolidine)-
      Gly
<220> FEATURE:
<221> NAME/KEY: MOD_RES
<222> LOCATION: (32)
<223> OTHER INFORMATION: Xaa = Leu coupled via thioester to PAM resin

<400> SEQUENCE: 7

Xaa Ala Val Val Phe Val Thr Arg Lys Asn Arg Gln Val Ser Ala Asn
 1               5                  10                  15

Pro Glu Lys Lys Ala Val Arg Glu Tyr Ile Asn Ser Leu Glu Leu Xaa
            20                  25                  30
```

CHEMICAL PEPTIDE LIGATION WITH THREE OR MORE COMPONENTS

FIELD OF THE INVENTION

The invention relates generally to methods for synthesizing polypeptides and proteins, and more particularly, to a method and intermediates for covalently assembling multiple peptide fragments into a full length polypeptide.

BACKGROUND

The sequencing of the human genome has created the promise and opportunity for understanding the function of all genes and proteins relevant to human biology and disease, Peltonen and McKusick, Science, 291: 1224-1229 (2001). However, several important hurdles must be overcome before this promise can be fully attained. First, even with the human genome sequence available, it is still difficult to distinguish genes and the sequences that control their expression. Second, although monitoring gene expression at the transcript level has become more robust with the development of microarray technology, a great deal of variability and control of function originates in post-transcriptional events, such as alternative splicing and post-translational processing and modification. Finally, because of the scale of human molecular biology (about a third of the estimated 30-40 thousand genes appear to give rise to multiple splice variants and most appear to encode protein products with a plethora of post-translational modifications), potentially many tens of thousands of genes and their expression products will have to be isolated and tested in order to understand their role in health and disease, Dawson and Kent, Annu. Rev. Biochem., 69: 923-960 (2000).

In regard to the issue of scale, the application of conventional recombinant methodologies for cloning, expressing, recovering, and isolating proteins is still a time consuming and labor-intensive process, so that its application in screening large numbers of different gene products for determining function has been limited. Recently, a convergent synthesis approach has been developed which may address the need for facile access to highly purified research-scale amounts of protein for functional screening, Dawson and Kent (cited above); Dawson et al, Science, 266: 776-779 (1994). In its most attractive implementation, an unprotected oligopeptide intermediate having a C-terminal thioester reacts with an N-terminal cysteine of another oligopeptide intermediate under mild aqueous conditions to form a thioester linkage which spontaneously rearranges to a natural peptide linkage, Kent et al, U.S. Pat. No. 6,184,344. The approach has been used to assemble oligopeptides into active proteins both in solution phase, e.g. Kent et al, U.S. Pat. No. 6,184,344, and on a solid phase support, e.g. Canne et al, J. Am. Chem .Soc., 121: 8720-8727 (1999) and U.S. Pat. No. 6,326,468. Recently, the technique has been extended to permit coupling of C-terminal thioester fragments to a wider range of N-terminal amino acids of co-reactant peptides by using a removable ethylthio moiety attached to the N-terminal nitrogen of the co-reactant, thereby mimicking the function of an N-terminal cysteine, Low et al, Proc. Natl. Acad. Sci., 98: 6554-6559 (2001).

Unfortunately, when the polypeptide to be synthesized by this approach exceeds 100-150 amino acids, it is usually necessary to join three or more fragments, as it is currently difficult to synthesize and purify oligopeptide intermediates longer than about 60 residues. In this case, the internal oligopeptide intermediates not only contain a C-terminal thioester moiety, but also an N-terminal cysteine. During the assembly process, the cysteine or cysteine-mimic of such internal intermediates, if left free, will react with the C-terminal thioester of the same intermediate molecule or that of a different intermediate molecule, thereby interfering with the desired ligation reaction by the formation of an undesired cyclical peptide or concatemer of the intermediate. This problem can be circumvented by employing a protecting group for the N-terminal amino acid with the following properties: i) it must be stable to the conditions used to synthesize and cleave the oligopeptide from the synthesis resin, ii) it must be removable after a native chemical ligation has been completed, and iii) preferably, removal takes place in the same ligation reaction mixture before purification, so that the ligation reaction and amino acid deprotection can be conducted in one pot.

The extension of the chemical ligation methodology by the use of auxiliary groups on the N-terminal amino acids of peptide reactants has given rise to a need for the effective protection groups for this class of reagents as well as methods for their synthesis and use.

SUMMARY OF THE INVENTION

In view of the above, objects of the invention include, but are not limited to, providing a method for convergent synthesis of polypeptides; providing oligopeptide intermediates that can undergo native chemical ligation to form a polypeptide product in a multi-component synthesis, but that are resistant to self-ligation and concatemerization; providing a heterocyclic protecting group for N-terminal amino acid residues of oligopeptide intermediates of native chemical ligation reactions; providing a method of protecting thioester-modified oligopeptide intermediates from self-ligations or concatemerizations; providing a method of temporarily blocking in either solid or solution phase the N-terminal residue of an oligopeptide thus providing at the same time a purification and protection tool; and providing a method for native chemical ligation of successive oligopeptide intermediates in a single reaction mixture.

The present invention provides a method of synthesizing a polypeptide by ligation of three or more oligopeptide intermediates, the method comprising the steps of:

(a) forming a ligation product having an N-terminal amino acid with a heterocyclic protecting group by reacting an N-terminal heterocyclic-protected oligopeptide having a C-terminal thioester with a prior ligation product under conditions that permit the formation of an amide bond between an α-carbon of the C-terminal thioester and an α-carbon of the N-terminal amino acid of the prior ligation product;

(b) treating the ligation product with a nucleophilic agent under acidic conditions to open the heterocyclic protecting group to form a prior ligation product with a free N-terminal cysteine or a secondary N-terminal amine having an auxiliary group, the auxiliary group having the form -D-SH, wherein D is an alkyl, alkenyl, aryl, aralkyl, or cycloalkyl linking moiety having from 2 to 16 carbon atoms and from 0 to 4 heteroatoms selected from the group consisting of O, S, and P;

(c) repeating steps (a) and (b) until a polypeptide having one or more auxiliary groups is formed; and (d) removing the one or more auxiliary groups to form the desired polypeptide;

(e) wherein steps (a) and (b) are optionally performed on a solid support.

The invention accomplishes these and other objectives by providing a heterocyclic protecting group for modified N-terminal amino acids of internal thioester-modified oligopeptide intermediates of native chemical ligation reactions. Among the uses of the protecting group of the invention is a solid phase-based chemical ligation method which allows an enhancement of the ligation reaction by using one reagent in excess, and subsequently purifying reacted materials, e.g. by washing out the unreacted excess reagent. These techniques were made possible in a field of use limited to Cysteine residues in the disclosures of PCT applications WO 01/81367 and PCT/IB02/02949, but the present invention provides a means to use them with any N-terminal amino acid residues. Furthermore, such solid phase-based chemical ligation methods are useful for the synthesis of proteins which contain synthesis fragments which are difficult to solubilize on their own, but which fold into a soluble polypeptide once they are ligated to other synthesis fragments. By providing a means of attaching those synthesis fragments with decreased solubility to a solid support, the present invention solves the temporary solubility problem by spatially separating those fragments that have a tendency to self aggregate, until they are ligated with other fragments to form a soluble polypeptide. Preferably, the heterocyclic-protected internal thioester-modified intermediates of the invention are described by Formula I:

FORMULA 1

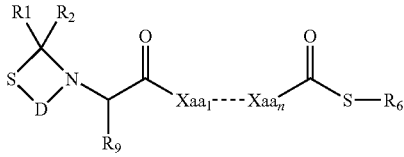

wherein:

each of $Xaa_1$ to $Xaa_\alpha$ is independently a protected or unprotected amino acid;

n is an integer from 2 to 120, more preferably, from 2 to 70, and still more preferably, from 2 to 50;

$R_1$ and $R_2$ are selected to promote the opening of the heterocycle of Formula I under acidic conditions in the presence of a nucleophilic agent, as described more fully below. Preferably, $R_1$ and $R_2$ are separately hydrogen, substituted or unsubstituted alkyl, electron withdrawing-substituted alkyl having from 1 to 3 carbon atoms, arylcarbonyl having 2 to 3 carbon atoms, or arylcarbonyl having 7 to 10 carbon atoms wherein $R_1$ or $R_2$ may optionally be attached to a solid support.

D is a linking moiety that together with a free sulfhydryl resulting from the opening of the heterocycle of Formula I after deprotection (described more fully below) is referred to herein as an "auxiliary group." That is, the structure "HS-D-" is referred to herein as an auxiliary group. Preferably D is an alkyl, alkenyl, aryl (including aryl groups that can form a fused bicyclic with the heterocylcle of Formula I), aralkyl (including benzyl), cycloalkyl (including cycloalkyl groups that can form a fused bicyclic with the heterocylcle of Formula I)moiety consisting of from 2 to 16 carbon atoms and from 0 to 4 heteroatoms that (i) maintains the heterocyclic sulfur of Formula I closely adjacent to the heterocylic nitrogen of Formula I after deprotection in order to promote the rearrangement reaction of native chemical ligation and (ii) provides a cleavable bond to the heterocyclic nitrogen of Formula I so that after deprotection and fragment ligation (coupling) the auxiliary group may be removed. Preferably, whenever in the form "HS-D," D maintains the sulfhydryl group within an equivalent distance of 2 to 3 carbon-carbon bond lengths of the $N^\alpha$ of the N-terminal amino acid of Formula I, the carbon-carbon bonds being those of a linear alkyl group. Preferably, D maintains the sulfhydryl group within a distance of 1.54 to 6.50 Å of the $N^\alpha$ of the N-terminal amino acid of Formula I.

$R_6$ is alkyl having from 1 to 6 carbon atoms, alkylaryl having from 6 to 8 carbon atoms, —$CH_2$—$CONH_2$, —$CH_2CH_2CONH_2$, or —$(CH_2)_k$—CO-Xaa, wherein k is an integer equal to 1 or 2 and Xaa is an amino acid.

$R_9$ is an amino acid side chain, except for those of proline or cysteine; and more preferably, except for those of proline, cysteine, valine, isoleucine, or threonine. In further preference, $R_9$ is hydrogen, methyl, or the side chain of histidine; and most preferably, $R_9$ is hydrogen or methyl.

Either $R_1$ or $R_2$ is optionally attached to a solid support. Methods of attachment are exemplified in Example 4 and FIG. 7 herein. Further methods of attachment are described, for example, in PCT/GB01/01803 (WO01/18367). It will be appreciated, however, that any suitable method of attachment of a chemical compound to a solid support may be used.

More preferably, the heterocyclic protecting group of the invention is a 1,3-thiazolidine, 1,3-thiazinane, or a saturated heterocycle containing three carbon atoms, one nitrogen atom, one sulfur atom, the sulfur atom being separated from the nitrogen atom by one to three (preferably one) carbon atoms (in the most direct route around the heterocycle), and a heteroatom selected from the group consisting of nitrogen, oxygen, sulfur, and phosphorus (preferably oxygen, sulfur, and phosphorus), the heteroatom being directly bonded to the nitrogen atom. Preferably, such heterocyclic-protected internal thioester-modified intermediates of the invention are described by Formulas II through IV:

FORMULA II

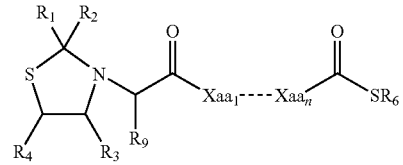

FORMULA III

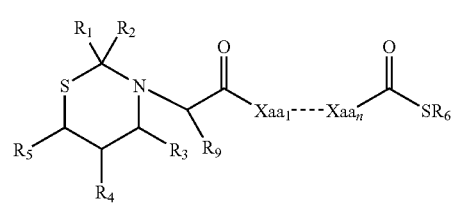

FORMULA IV

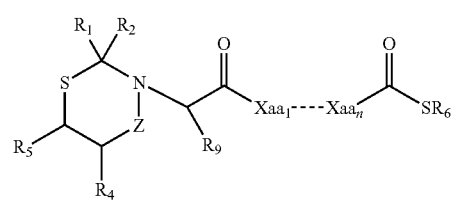

wherein:

$R_1$, $R_2$, $R_4$ and $R_9$ are described as above.

$R_3$ taken alone is hydrogen or an electron donating group having from 1 to 12 carbon atoms and from 0 to 4 heteroatoms selected from the group consisting of nitrogen, oxygen, sulfur, and phosphorus; preferably, $R_3$ taken alone is hydrogen or electron donating group having from 1 to 8 carbon atoms and from 0 to 2 heteroatoms selected from the group consisting of nitrogen, oxygen, and sulfur, still more preferably, $R_3$ taken alone is hydrogen, phenyl electron donating-substituted phenyl 2- or 4-picolyl, or electron donating-substituted 2- or 4-picolyl; still more preferably, $R_3$ taken alone is hydrogen or methoxy-substituted phenyl; most preferably, $R_3$ taken alone is 4-methoxyphenyl or 2,4-dimethoxyphenyl.

$R_4$ and $R_5$ taken alone are independently each hydrogen, alkyl having from 1 to 3 carbon atoms, aryl or electron donating-substituted aryl having 6-10 carbon atoms with 0-2 heteroatoms, or electron donating-substituted alkyl having from 1 to 3 carbon atoms; preferably, $R_4$ and $R_5$ taken alone are independently each hydrogen, alkyl having from 1 to 3 carbon atoms, or electron donating-substituted alkyl having from 1 to three carbon atoms; more preferably, $R_4$ and $R_5$ taken alone are each hydrogen.

$R_4$ and $R_3$, when taken together with the 2- and 3-carbons in either the heterocyclic ring of Formula II or the heterocyclic ring of Formula III, are alkyl having 3 to 20 carbon atoms, or aryl or electron donating-substituted aryl having 6 to 10 carbon atoms with 0-2 heteroatoms; preferably, $R_4$ and $R_3$, when taken together with the 2- and 3-carbons in either the heterocyclic ring of Formula II or the heterocyclic ring of Formula III, are aryl or electron donating-substituted aryl having 6 to 10 carbon atoms with 0-2 heteroatoms; more preferably, $R_4$ and $R_3$, when taken together with the 2- and 3-carbons in either the heterocyclic ring of Formula II or the heterocyclic ring of Formula III, are methoxy-substituted aryl having 7-8 carbon atoms.

$R_4$ and $R_5$, when taken together with the 3- and 4-carbons in either the heterocyclic ring of Formula III or the heterocyclic ring of Formula IV are alkyl having 3 to 20 carbon atoms, or aryl or electron donating-substituted aryl having 6 to 10 carbon atoms; preferably, when taken together with the 3- and 4-carbons in either the heterocyclic ring of Formula III or the heterocyclic ring of Formula IV are aryl or electron donating-substituted aryl having 6 to 10 carbon atoms; more preferably, $R_4$ and $R_5$, when taken together with the 3- and 4-carbons in the heterocyclic ring of Formula III or IV are methoxy-substituted aryl having 7-8 carbon atoms. Preferably, $R_3$ and $R_4$ are not taken together at the same time as $R_4$ and $R_5$.

Z is a heteroatom selected from the group consisting of O, S, N and P, preferably O, S and P.

In a preferred embodiment of the compounds, compositions and methods of the present invention $R_1$ is hydrogen and $R_2$ is electron withdrawing-substituted alkyl having from 1 to 3 (preferably 1) carbon atoms.

As used herein, "electron withdrawing" refers to the tendency of a substituent to attract valence electrons from the molecule to which it is attached, i.e. it is electronegative, and "electron donating" refers to the tendency of a substituent to donate valence electrons to the molecule to which it is attached, i.e. it is electropositive, e.g., Smith and March, March's Advanced Organic Chemistry: Reactions, Mechanisms, Structure, 5th Edition (Wiley-Interscience, New York, 2001). A mild electron donating group refers to a group with limited propensity to donate valence electrons to the molecule to which it is attached. Such effect could be due either to the presence of a single group like the alkenyl or alkyl substituent where the "electron donating" feature is more an inductive effect rather than an effective capability to transfer valence electrons or to the combined effect of electron donating and electron withdrawing of two or more moieties where the electron donating effect is prevailing. A mild electron withdrawing group refers to a group with limited tendency to attract valence electrons from the molecule to which it is attached. Such effect could be due either to the mild electron withdrawing effect of a single group or to the combined effect of electron donating and electron withdrawing properties of a single substituent or to the combined effect of electron donating and electron withdrawing properties of two or more entities where the electron withdrawing effect is prevailing. Preferred electron withdrawing substituents include but are not limited to, halo- (especially mono and poly (including di- and tri-) chloro, bromo and fluoro), cyano, or nitro-substituted alkyl having from 1 to 3 carbon atoms, carbonyl, carboxy, carboxyester, carboxyamide, amidocarboxy, amidocarbonyl, sulfoxy, sulfone and quaternary ammonium salts, or alkyl groups from 1 to 3 carbon atoms bearing any of the above electron withdrawing moieties, and a combination of electron donating and electron withdrawing properties of two or more entities where the electron withdrawing effect is prevailing In one preferred embodiment electron withdrawing substituents are substituted carboxy amide, carboxyester, amidocarboxy, amidocarbonyl or alkyl groups with 1 carbon atom with any of the above electron withdrawing moieties. In another preferred embodiment electron withdrawing substituents include halo-, especially chloro and bromo, cyano, or nitro-substituted allyl having from 1 to 3 carbon atoms; more preferably, electron withdrawing substituents are halo-substituted methyl. Preferred electron donating substituents include alkyl having from 1 to 100 carbon atoms, alkenyl, methoxy, thiol, hydroxyl, amino, alkylamino, methylthio, alkylthio, aryl, heterocyclic, heteroaromatics with 1 to 4 heteroatoms, aralkyl comprising 1 to 8 alkyl aliphatic atoms attached to an aryl group, benzyl and a combination of electron donating and electron withdrawing properties of two or more entities where the electron donating effect is prevailing. In one preferred embodiment, electron donating substituents are alkyl, alkenyl benzyl, aryl, methoxy, thiol, methylthio, or hydroxyl. In another preferred embodiment, preferred electron donating substituents include alkyl having from 1 to 3 carbon atoms, methoxy, thiol, hydroxyl, and methylthio; more preferably, electron donating substituents are methoxy, thiol, methylthio, or hydroxyl. Preferably, whenever a substituent is substituted with electron donating group, such as electron donating- or electron-withdrawing-substituted phenyl, between 1 and 3 such groups are attached; more preferably, between 1 and 2 such groups are attached.

Another aspect of the invention are derivatized amino acid compositions, useful in the synthesis of the heterocyclic-protected oligopeptide thioesters, of the formula

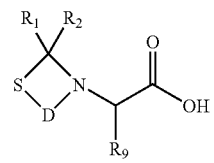

wherein $R_1$, $R_2$ and $R_9$ are described as above.

Preferably, such derivatized amino acid compositions are selected from the group consisting of the formulae

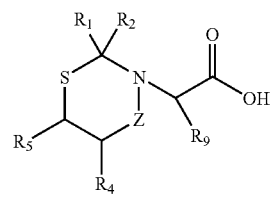

-continued

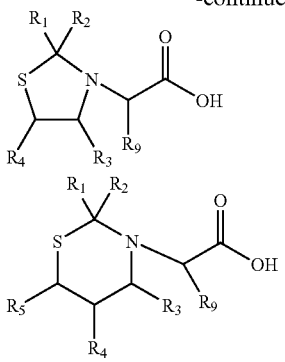

wherein $R_1$, $R_2$, $R_3$, $R_4$, $R_5$, $R_9$ and Z are described as above.

Preferably, such derivatized amino acid compositions are selected from the group consisting of 1,3-thiazolidine-, 1,3-thiazinane-, and 1,4,2oxathiazinane-protected amino acids of the formulas:

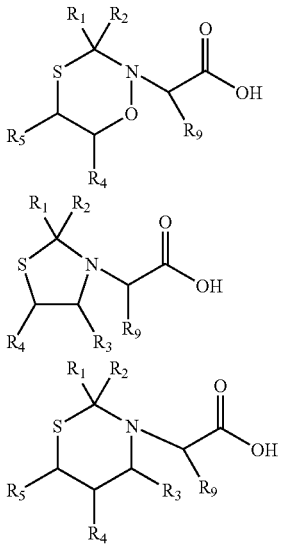

wherein $R_1$, $R_2$, $R_3$, $R_4$, $R_5$ and $R_9$ are described as above. More preferably, derivatized amino acids of the invention are 1,3-thiazolidine-protected amino acids of the following formula:

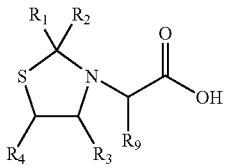

wherein $R_1$ and $R_2$ are separately hydrogen or methyl; $R_3$ taken alone is hydrogen or an electron donating group having from 1 to 12 carbon atoms and from 0 to 4 heteroatoms selected from the group consisting of nitrogen, oxygen, and sulfur; $R_4$ taken alone is hydrogen, alkyl having from 1 to 3 carbon atoms, or electron donating-substituted alkyl having from 1 to 3 carbon atoms; alternatively, $R_4$ and $R_3$, taken together with the 2- and 3-carbons in the 1,3-thiazolidine ring are aryl or electron donating-substituted aryl having 6 to 10 carbon atoms with 0-2 heteroatoms; $R_9$ is a side chain of an amino acid selected from the group consisting of alanine, aspartic acid, glutamic acid, phenylalanine, glycine, histidine, lysine, leucine, methionine, asparagines, glutamine, arginine, serine, tryptophan, and tyrosine. Still more preferably, $R_3$ taken alone is hydrogen, phenyl, electron donating-substituted phenyl, 2-picolyl, 4-picolyl, electron donating-substituted 2-picolyl, or electron donating-substituted 4-picolyl; $R_4$ taken alone is hydrogen; and $R_9$ is a side chain of an amino acid selected from the group consisting of glycine, alanine, and histidine. Most preferably, $R_3$ taken alone is hydrogen or methoxy-substituted phenyl.

In accordance with the method of the invention, a polypeptide is synthesized from three or more oligopeptide intermediates by the following steps: (i) forming a ligation product with an N-terminal heterocyclic-protected amino acid by reacting an internal oligopeptide intermediate with a prior ligation product under conditions that permit the formation of an amide bond between an α-carbon of a C-terminal thioester amino acid of the internal oligopeptide intermediate and an α-carbon of the N-terminal amino acid of the prior ligation product; (ii) treating the ligation product with a nucleophilic agent under acidic conditions to form a prior ligation product with a free N-terminal cysteine or a prior ligation product with a secondary N-terminal amine having an auxiliary group; (iii) repeating steps (i) and (ii) until a polypeptide having one or more auxiliary groups is formed; and (iv) removing the one or more auxiliary groups to form the desired polypeptide. Preferably, all of the auxiliary groups are removed simultaneously at the completion of polypeptide synthesis.

An aspect of the invention is the deprotection of the N-terminal amino acid by opening the N-terminal heterocyclic ring of the ligation product with a nucleophilic agent under acidic conditions after ligation and in the same reaction mixture to form a secondary N-terminal amine with an auxiliary group, or an N-terminal cysteine when cysteine is the N-terminal amino acid. Such agents include, but are not limited to, O-alkoxyhydroxylamines and hydrazines. Preferably, thiazolidine-protected N-terminal cysteines are deprotected by treatment with an O-alkoxyhydroxylamine under acidic conditions. More preferably, such O-alkoxyhydroxylamine deprotection agent has a formula: $H_2N$—O—R, where R is methyl, ethyl, isopropyl, isobutyl, or —$CH_2$—COOH. Preferably, R is methyl. Preferably, the acidic conditions include a pH in the range of from 2.0 to 6.0. More preferably, such pH is in the range of from 3.0 to 4.0.

Another aspect of the invention is the concomitant protection and purification scheme obtainable by solid support immobilization of the reactive 1,2 or 1,3 N-terminal amino thiol oligopeptide. As demonstrated by Matteo Villain, Jean Vizzavona and Keith Rose, Chem Biol. 2001 July; 8(7):673-9, Keith Rose Matteo Villain, Jean Vizzavona, International Patent Application PCT/GB01/01803 (WO01/18367) the N-terminal 1,2 amino thiol of a native cysteinyl polypeptide can be selectively immobilized and self-purified on a solid support through reversible thiazolidine ring formation. Since the process of covalent capture as described above by Villain et al. takes place in acidic medium, conditions under which N-terminal 1,2 or 1,3 amino thiol and thioester functionalities are mutually unreactive, it is then applicable to fragments bearing both N-terminal 1,2 or 1,3 amino thiol and thioester functionality on the same molecule.

The present invention is useful in methods for convergent synthesis of polypeptides and proteins and advantageously addresses limitations in these methodologies. In particular, it provides a method and materials for improving the efficiency of native chemical ligation reactions used to assemble thioester-modified oligopeptide intermediates into polypeptides or proteins, particularly in such reactions involving more than two components.

BRIEF DESCRIPTION OF THE FIGURES

FIG. 8A is a chromatogram of the starting material from a ligation of a heterocyclic-protected oligopeptide thioester and a model oligopeptide (T=0).

DEFINITIONS

Figure 1:
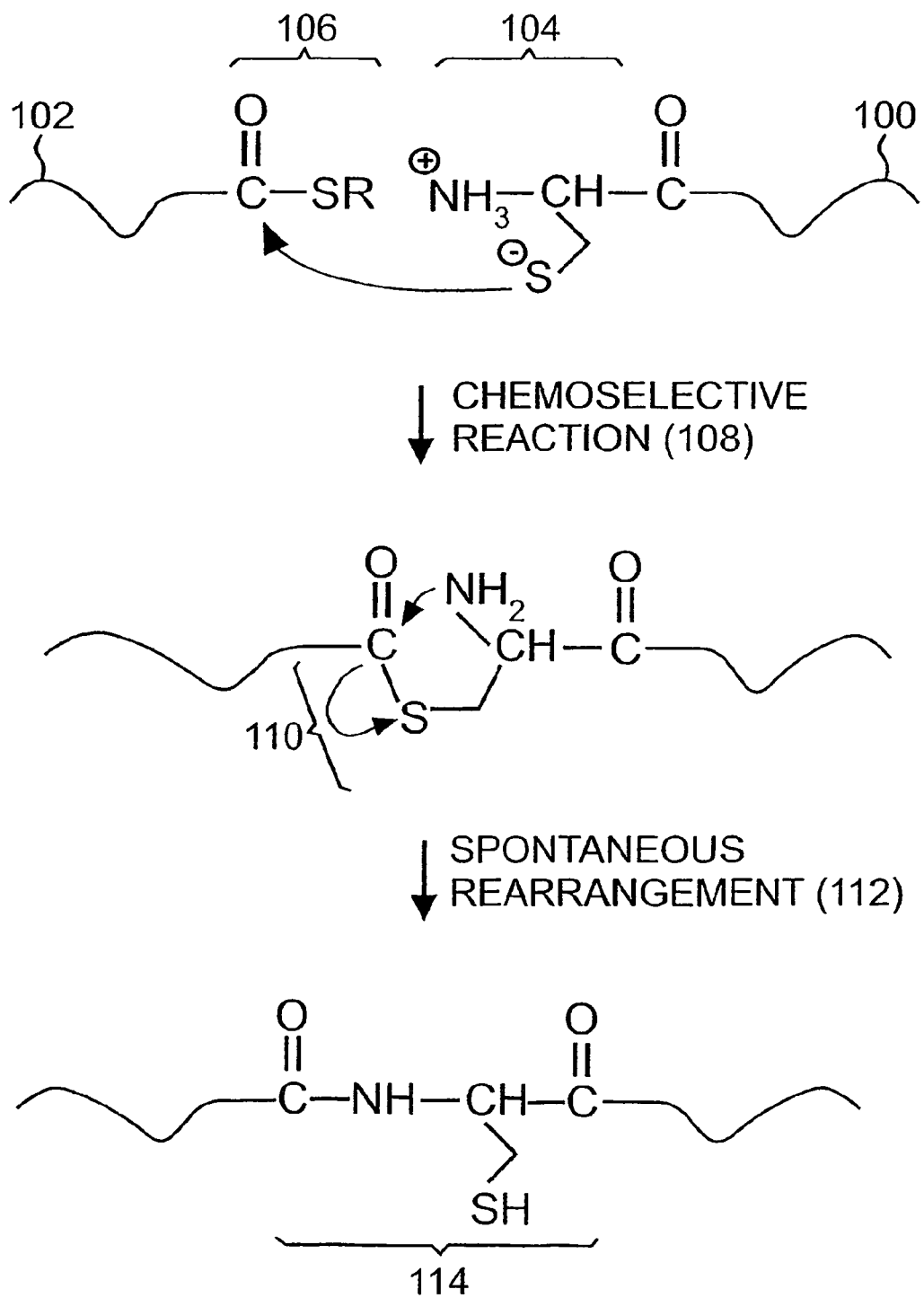
FIG. 1 illustrates native chemical ligation wherein the co-reactant of the thioester-modified oligopeptide is an oligopeptide with an N-terminal cysteine.

The terms "polypeptide," "peptide," "peptide fragment," "oligopeptide," or "fragment" in reference to a peptide, as used herein refers to a compound made up of a single unbranched chain of amino acid residues linked by peptide bonds. The number of amino acid residues in such compounds varies widely; however, preferably, peptides or oligopeptides referred to herein usually have from 2 to 70 amino acid residues; and more preferably, they have for 2 to 50 amino acid residues. Polypeptides and peptide fragments referred to herein usually have from a few tens of amino acid residues, e.g. 20, to up to a few hundred amino acid residues, e.g. 200, or more.

The term "protein" as used herein may be used synonymously with the term "polypeptide" or may refer to, in addition, a complex of two or more polypeptides which may be linked by bonds other than peptide bonds, for example, such polypeptides making up the protein may be linked by disulfide bonds. The term "protein" may also comprehend a family of polypeptides having identical amino acid sequences but different post-translational modifications, such as phosphorylations, acylations, glycosylations, and the like, particularly as may be added when such proteins are expressed in eukaryotic hosts.

Amino acid residues are referred to herein by their standard single-letter or three-letter notations: A, alanine; C, cysteine; D, aspartic acid; E, glutamic acid; F, phenylalanine; G, glycine; H, histidine; I, isoleucine; K, lysine; L, leucine; M, methionine; N, asparagine; P, proline; Q, glutamine; R, arginine; S, serine; T, threonine; V, valine; W, tryptophan; Y, tyrosine. An amino acid sequence set forth herein, such as "DKLLM" (SEQ ID NO:5), orders the amino acids from the N-terminus to the C-terminus in a left-to-right manner, unless otherwise indicated from the context.

As used herein, the term "amino acid side chain" refers to the substituent at the a carbon atom of an amino acid.

As used herein except where otherwise defined, the term "heteroatom" refers to an atom selected from O, N, S and P.

As used herein except where otherwise defined, the term "heterocyclic" refers to an optionally substituted, aromatic or non-aromatic hydrocarbon ring of 4-20, more preferably 5-10 carbon atoms and 1 to 4 heteroatoms. As used herein except where otherwise defined, the term "heteroaromatic" refers to an optionally substituted, aromatic hydrocarbon ring of 4-20, more preferably 5-10 carbon atoms and 1 to 4 heteroatoms. A heterocyclic or heteroaromatic group may be substituted with 0-3 substituents selected from groups including, but not limited to, halo- (especially mono and poly (including di- and tri-) chloro, bromo and fluoro), cyano, nitro, carbonyl, carboxy, carboxyester, carboxyamide, amidocarboxy, amidocarbonyl, sulfoxy, sulfone and quaternary ammonium salts, alkyl alkenyl methoxy, thiol, hydroxyl, amino, alkylamino, methylthio, alkylthio, aryl, heterocyclic, aralkyl as comprising 1 to 8 alkyl aliphatic atoms attached to an aryl group (such as benzyl) or alkyl groups from 1 to 3 carbon atoms bearing any of the above moieties.

As used herein except where otherwise defined, the term "alkyl" refers to a branched or unbranched, optionally substituted, saturated or unsaturated (i.e. including alkenyl and alkynyl) hydrocarbon chain of 1-100, preferably 1-20, more preferably 1-6, more preferably 1-3, more preferably 1, carbon atom. An alkyl group may be substituted with 0-3 substituents selected from groups including, but not limited to, halo- (especially mono and poly (including di- and tri-) chloro, bromo and fluoro), cyano, nitro, carbonyl, carboxy, carboxyester, carboxyamide, amidocarboxy, amidocarbonyl, sulfoxy, sulfone and quaternary ammonium salts, alkenyl, methoxy, thiol, hydroxyl, amino, alkylamino, methylthio, alkylthio, aryl, heterocyclic, heteroaromatics with 1 to 4 heteroatoms, aralkyl as comprising 1 to 8 alkyl aliphatic atoms attached to an aryl group (such as benzyl) or aryl groups bearing any of the above moieties. It will be appreciated that as used herein the term "alkyl" includes, as the context requires, reference to either or both monovalent alkyl groups and divalent alkyl or alkylene groups As used herein except where otherwise defined, the term "aryl" refers to an optionally substituted, aromatic hydrocarbon ring of 5-100, preferably 5-20, more preferably 5-10 carbon atoms. Preferred aryl groups include phenyl and naphthyl groups. An aryl group may be substituted with 0-3 substituents selected from groups including, but not limited to, halo- (especially mono and poly (including di- and tri-) chloro, bromo and fluoro), cyano, nitro, carbonyl, carboxy, carboxyester, carboxyamide, amidocarboxy, amidocarbonyl, sulfoxy, sulfone and quaternary ammonium salts, alkenyl, methoxy, thiol, hydroxyl, amino, alkylamino, methylthio, alkylthio, aryl, heterocyclic, heteroaromatics with 1 to 4 heteroatoms, aralkyl as comprising 1 to 8 alkyl aliphatic atoms attached to an aryl group (such as benzyl) or alkyl groups from 1 to 3 carbon atoms bearing any of the above moieties. It will be appreciated that as used herein the term "aryl" includes as the context requires reference to either or both monovalent aryl groups and divalent aryl or arylene groups.

As used herein except where otherwise defined, the term "aralkyl" refers to a group in which an aryl group is linked to an alkyl group and may be linked to the rest of a molecule via either the aryl or alkyl group. The term includes a benzyl group.

Detailed Description of the Invention

The invention relates to the assembly of oligopeptides into a polypeptide by the process of native chemical ligation, as described by Low et al, Proc. Natl. Acad. Sci., 98: 6554-6559 (2001) and Botti et al, Tetrahedron Letters, 42: 1831-1833 (2001). The general approach of native chemical ligation and its extension by Low et al and Botti et al is illustrated in FIG. 1. In the original native chemical ligation technique, e.g. as described by Dawson et al and Kent et al (cited in the Background), coupling of peptide fragments could take place only between an N-terminal cysteine and C-terminal thioester. As shown, a first oligopeptide (100) is provided with an N-terminal cysteine (104) having an unoxidized sulfhydryl side chain, and a second oligopeptide (102) is provided with a C-terminal thioester (106). In the coupling reaction (108), the unoxidized sulfhydryl side chain of the N-terminal cysteine is condensed with, the C-terminal thioester to produce an intermediate oligopeptide which links the first and second oligopeptides with a β-aminothioester bond (110). The β-aminothioester bond of the intermediate oligopeptide then undergoes an intramolecular rearrangement (112) to produce the oligopeptide product that links the first and second oligopeptides with amide bond (114).

Figure 2:
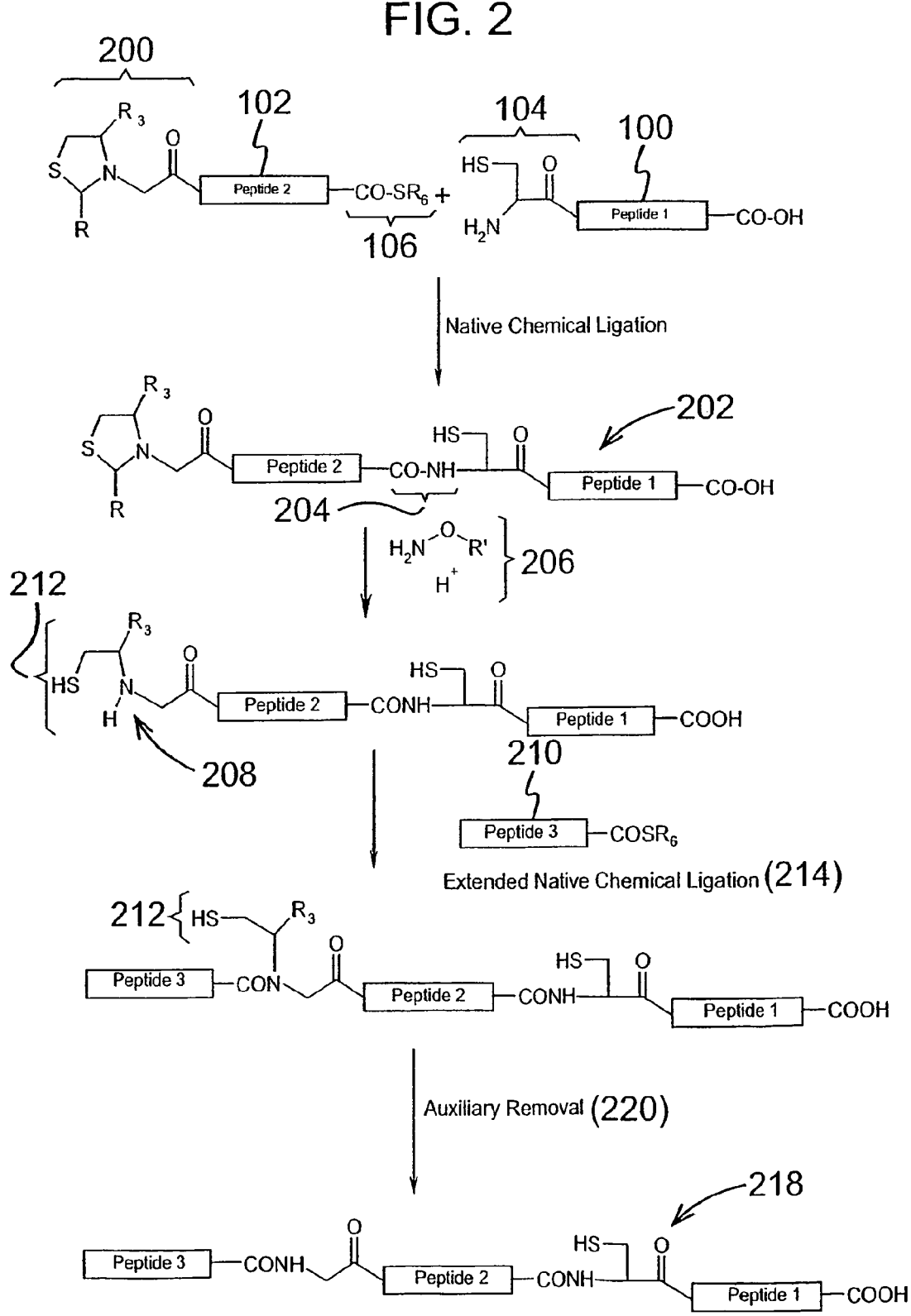
FIG. 2 illustrates native chemical ligation with the use of auxiliary groups ("extended native chemical ligation" using a heterocyclic-protected thioester-modified oligopeptide intermediate of the invention.

A problem arises in this scheme when a polypeptide is assembled from three or more fragments. In this situation, at least one fragment will have both an N-terminal cysteine and a C-terminal thioester, thereby creating the possibility for self-ligation, which under conventional reaction conditions is quite significant because of the close proximity of the reactive intra-molecular moieties. In view of this, the N-terminal cysteine of an internal fragment can protected from such reactions by a cyclic thiazolidine protecting group, as demonstrated by Gaertner et al, Proceedings of the 17$^{th}$ American Peptide Symposium, pgs. 107-108 (San Diego, Jun. 9-14, 2001). Until the present invention thereof, similar protecting groups were unavailable to chemical ligations using auxiliary groups, such as disclosed by Low et al and Botti et al. In accordance with the invention, a new class of heterocyclic protecting groups is provided that significantly increases the efficiency of ligations by preventing self-ligations in auxiliary groups-assisted ligations. The operation of the heterocyclic protecting groups of the invention is illustrated in FIG. 2 for a three component ligation. Heterocyclic-protected thioester-modified oligopeptide (102) has thioester group (106) and exemplary heterocyclic protecting group (200). Thioester (106) reacts with N-terminal cysteine (104) of oligopeptide (100) as described by Dawson et al, Kent et al, and others (cited above) to give ligation product (202) consisting of oligopeptide (100) and oligopeptide (102) conjugated by amide bond (204). The ligation product at this step is then treated with an O-alkoxyhydroxylamine (206) under acidic conditions to open heterocyclic protecting group (200) giving a free terminal sulfhydryl group on auxiliary group (212) attached to the secondary amine of the N-terminal amino acid (208), which in this illustration is glycine. After such deprotection, the next thioester-modified oligopeptide (210) reacts (214) with N-terminal amine (208) as taught by Low et al and Botti et al (cited above) to give intermediate product (216). Auxiliary group (212) is removed (220) by acid treatment to give final product (218). Preferably, such removal is accomplished by treatment with HF or trifluoroacetic acid (TFA). Exemplary removal conditions include (i) 95% HF and 5% p-cresol, (ii) TFA/bromotrimethylsilane, and (iii) 95% TFA, 2.5% triisopropylsilane (TIS), and 2.5% water.

Unless otherwise noted, these reactions and those described below take place at room temperature.

Figure 3:
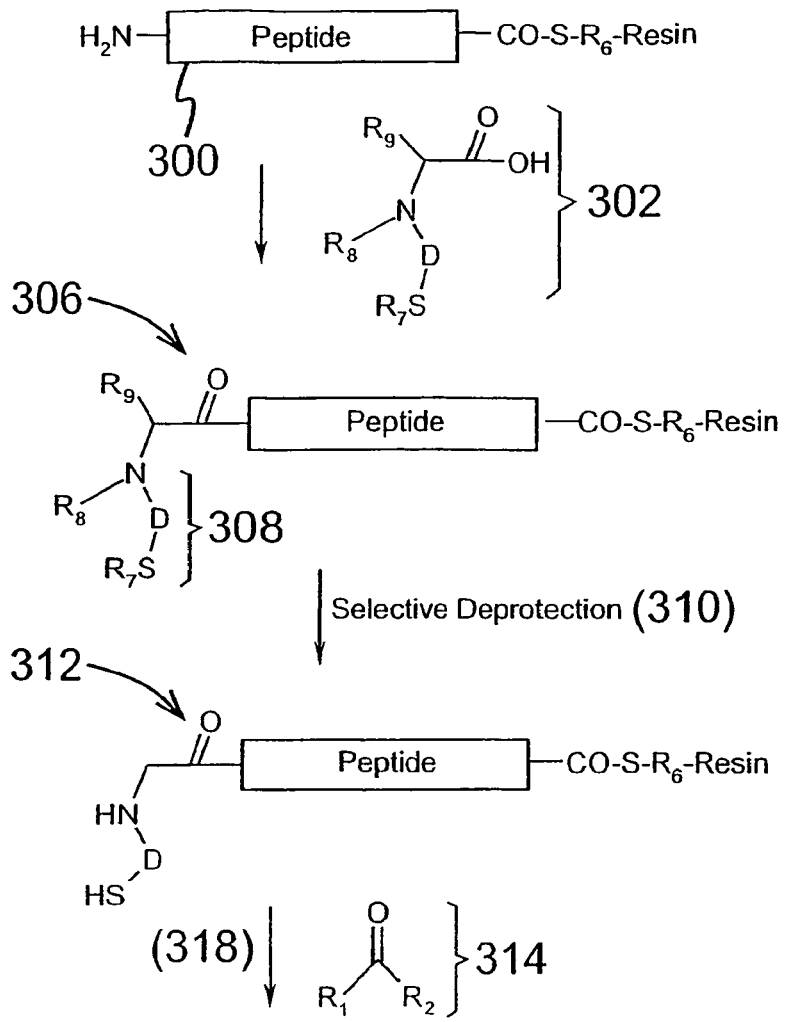
FIG. 3 illustrates scheme 1 for synthesizing heterocyclic-protected thioester-modified oligopeptide intermediates of the invention.
Figure 3:
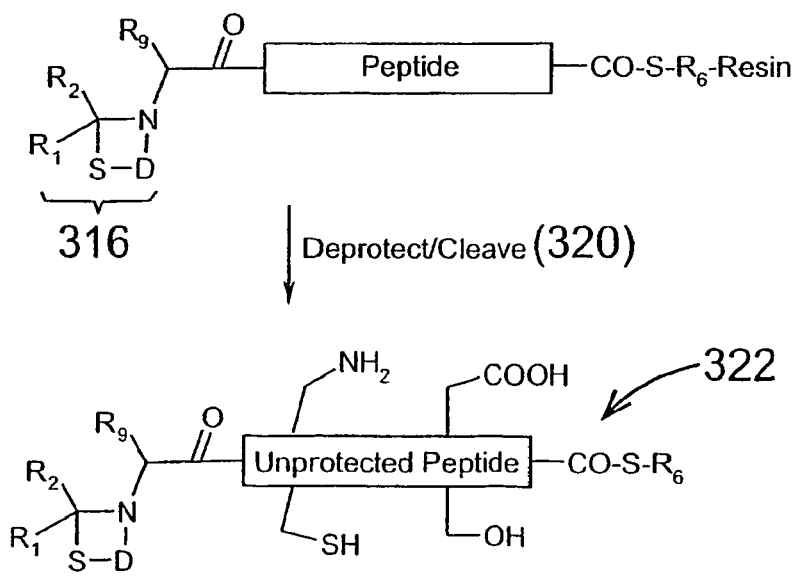
Figure 4:
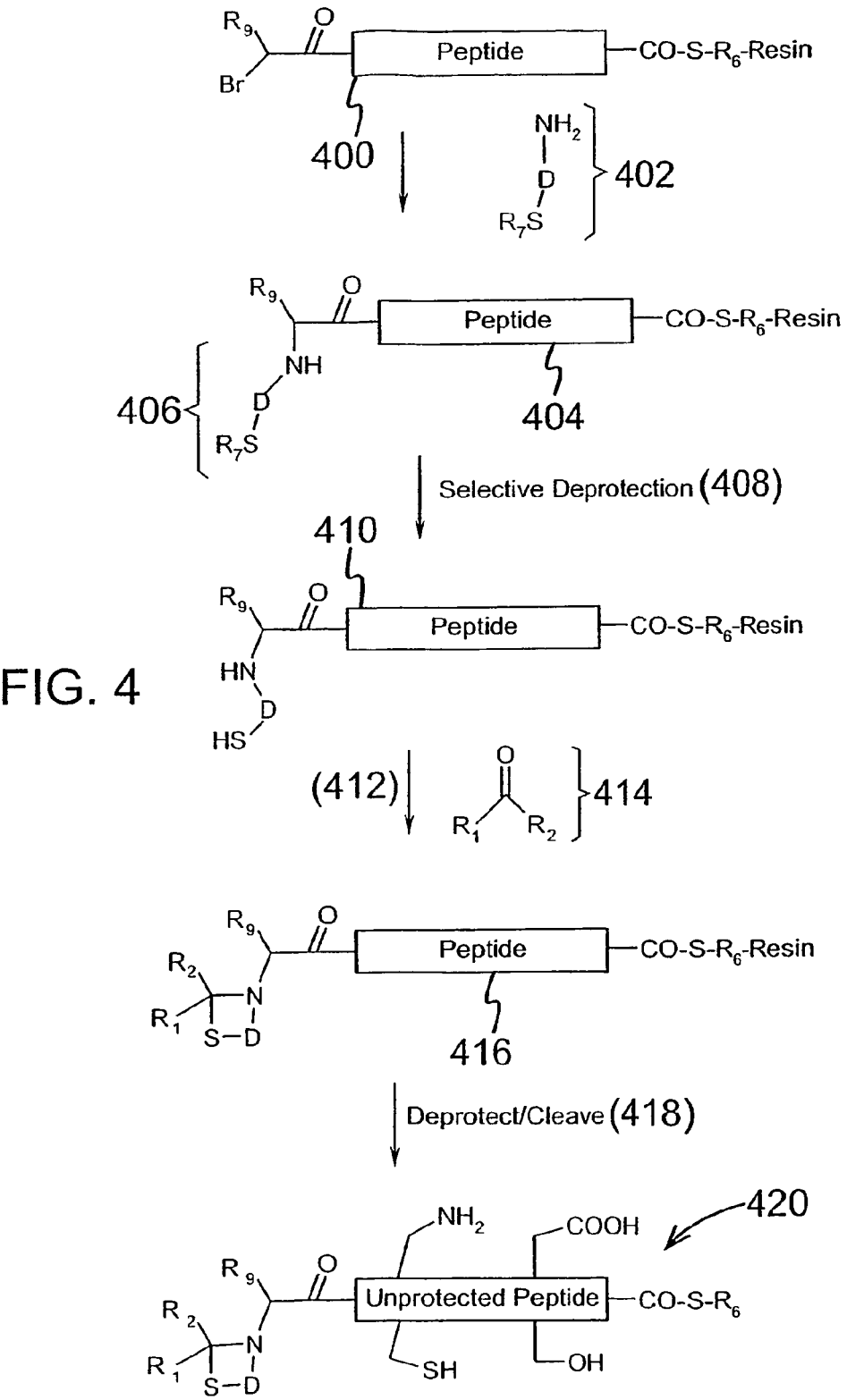
FIG. 4 illustrates scheme 2 for synthesizing heterocyclic-protected thioester-modified oligopeptide intermediates of the invention.
Figure 5:
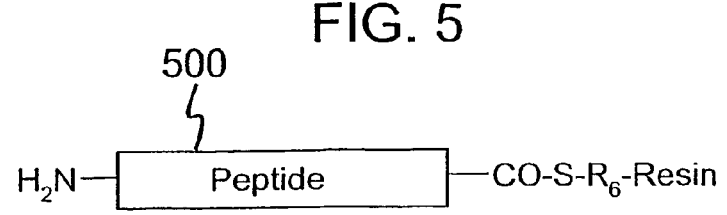
FIG. 5 illustrates scheme 3 for synthesizing heterocyclic-protected thioester-modified oligopeptide intermediates of the invention.
Figure 5:
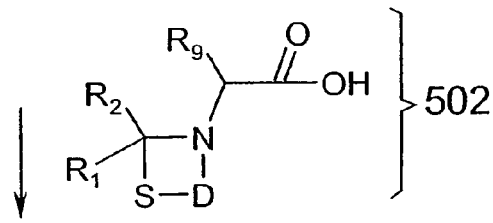
Figure 5:
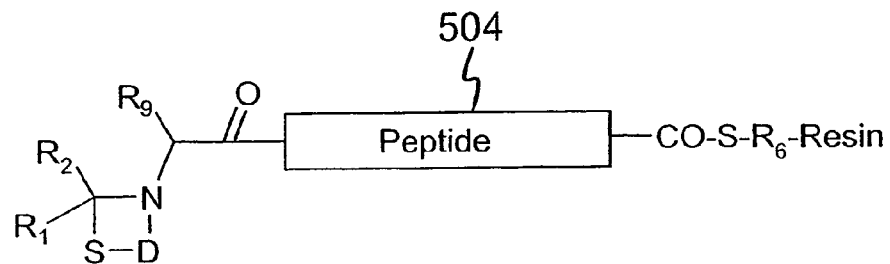
Figure 5:
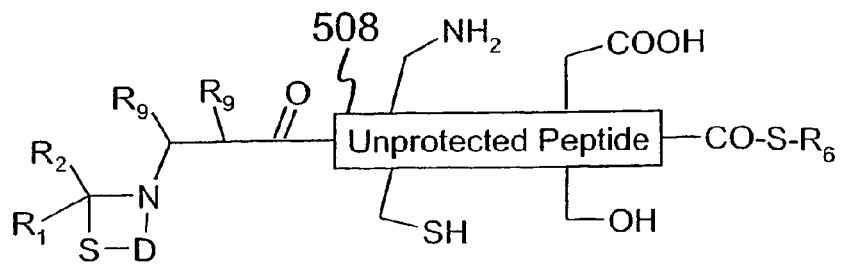

The heterocyclic protecting group of the invention may be formed at the N-terminus of an oligopeptide thioester by first synthesizing the oligopeptide thioester with an auxiliary group followed by cyclization of the free sulfhydryl of the auxiliary group with the secondary α-amine of the terminal amino acid. An oligopeptide thioester having an auxiliary group may be synthesized in several ways, including by halogen-mediated amino alkylation and reductive amination. Alternatively, the heterocyclic protecting group of the invention may be formed by preparation of a fully protected amino acid monomer with the heterocyclic protecting group in place for the last addition cycle in the synthesis of a desired oligopeptide thioester. Generally, however, synthesis begins with an oligopeptide thioester attached to a resin, as shown in FIGS. 3-5.

Oligopeptides having a C-terminal thioester (Peptide 2 (102) of FIG. 1) may be produced as described in the following references, which are incorporated by reference: Kent et al, U.S. Pat. No. 6,184,344; Tam et al, Proc. Natl. Acad. Sci., 92: 12485-12489 (1995); Blake, Int. J. Peptide Protein Res., 17: 273 (1981); Canne et al, Tetrahedron Letters, 36: 1217-1220 (1995); Hackeng et al, Proc. Natl. Acad. Sci., 94: 7845-7850 (1997); or Hackeng et al, Proc. Natl. Acad. Sci., 96: 10068-10073 (1999); Ingenito et al, J. Am. Chem. Soc., 121: 11369-11374 (1999). Preferably, the method described by Hackeng et al (1999) is employed. Briefly, oligopeptides are synthesized on a solid phase support (described below) typically on a 0.25 mmol scale by using the in situ neutralization/HBTU activation procedure for Boc chemistry disclosed by Schnolzer et al, Int. J. Peptide Protein Res., 40: 180-193 (1992), which reference is incorporated herein by reference. (HBTU is 2-(1H-benzotriazol-1-yl)-1,1,3,3-tetramethyluronium hexafluorophosphate and Boc is tert-butoxycarbonyl). Each synthetic cycle consists of N$^\alpha$-Boc removal by a 1- to 2-minute treatment with neat TFA, a 1-minute DMF flow wash, a 10- to 20-minute coupling time with 1.0 mmol of preactivated Boc-amino acid in the presence of DIEA, and a second DMF flow wash. (TFA is trifluoroacetic acid, DMF is N,N-dimethylformamide, and DIEA is N,N-diisopropylethylamine). N$^\alpha$-Boc-amino acids (1.1 mmol) are preactivated for 3 minutes with 1.0 mmol of HBTU (0.5 M in DMF) in the presence of excess DIEA (3 mmol). After each coupling step, yields are determined by measuring residual free amine with a conventional quantitative ninhydrin assay, e.g. as disclosed in Sarin et al, Anal. Biochem., 117: 147-157 (1981). After coupling of Gln residues, a DCM flow wash is used before and after deprotection by using TFA, to prevent possible high-temperature (TFA/DMF)-catalyzed pyrrolidone formation. Optionally, at the completion of chain assembly, a haloacetyl group, preferably bromoacetyl, may be added, as disclosed by Zuckerman et al, J. Am. Chem. Soc. 114: 10646-10647 (1992), which is incorporated by reference, as one route for synthesizing compounds of the invention.

Thioester oligopeptides may be synthesized using either Fmoc or Boc chemistries. When Fmoc chemistry is employed a 3-carboxypropanesulfonamide safety catch linker is used to generate the thioester. Thioester oligopeptides described above are preferably synthesized on a trityl-associated mercaptopropionic acid-leucine (TAMPAL) resin, made as disclosed by Hackeng et al (1999), or comparable protocol. Briefly, $N^\alpha$-Boc-Leu (4 mmol) is activated with 3.6 mmol of HBTU in the presence of 6 mmol of DIEA and coupled for 16 minutes to 2 mmol of p-methylbenzhydrylamine (MBHA) resin, or the equivalent Next, 3 mmol of S-trityl mercaptopropionic acid is activated with 2.7 mmol of HBTU in the presence of 6 mmol of DIEA and coupled for 16 minutes to Leu-MBHA resin. The resulting TAMPAL resin can be used as a starting resin for polypeptide-chain assembly after removal of the trityl protecting group with two 1 minute treatments with 3.5% triisopropylsilane and 2.5% $H_2O$ in TFA. The thioester bond can be formed with any desired amino acid by using standard in situ-neutralization peptide coupling protocols for 1 hour, as disclosed in Schnolzer et al (cited above). Treatment of the final oligopeptide with anhydrous HF yields the C-terminal activated mercaptopropionic acid-leucine (MPAL) thioester oligopeptides.

Preferably, oligopeptides thioesters are deprotected and cleaved from the resin by treatment with anhydrous HF for 1 hour at 0° C. with 4% p-cresol as a scavenger. The imidazole sidcahuin 2,4-dinitrophenyl (DNP) protecting groups remain on the His residues because the DNP-removal procedure is incompatible with C-terminal thioester groups. However, DNP is gradually removed by thiols during the ligation reaction. After cleavage, oligopeptide thioesters may be precipitated with ice-cold diethylether, dissolved in aqueous acetonitrile, and lyophilized.

Scheme 1 for synthesizing heterocyclic protected oligopeptide thioesters of the invention is shown in FIG. 3. In this scheme, a free N-terminal amine of oligopeptide thioester (300) is reacted with protected amino acid (302) with auxiliary group (-D-S—$R_7$) in a standard coupling reaction (304), e.g. Schnolzer et al (cited above), to give oligopeptide thioester (306) having auxiliary group (308) attached to the α-amine. $R_7$ is a sulfur-protecting group (preferably, an acid-labile one, more preferably, a "super-acid labile" one). Many sulfur protecting groups are known and useful for such purpose (see Protecting Groups in Organic Synthesis, 3rd Edition, T. W. Greene and P. G. M. Wuts, Eds. John Wiley & Sons, Inc., 1999, 455-493). Sulfur protecting groups include, but are not limited to, ACM (acetamidomethyl) and the like, Picolyl, Trityl and the like, Xanthyl, Phenacyl and the like, Benzyl, Fluorenylmethyl (FM) and the like and disulfide moieties. Preferred are electron donating substituted benzyl, ACM, Trityl, MethoxyTrityl, Xanthyl, Picolyl. Oligopeptide thioester (312) is formed by selective deprotection (310) of the α-amine and the sulfhydryl of the auxiliary group, after which it is reacted with substituted carbonyl (314) so that heterocyclic protecting group (316) is formed. Preferably, selective deprotection (310) is achieved by mild acid treatment, e.g. trifluoroacetic acid (TFA) under conventional reaction conditions, e.g. Green and Wuts (cited above), in the presence of a scavenger, such as triisopropylsilane (TIS), whenever $R_8$ is Boc, or like protecting group, and $R_7$ is triphenylmethyl, i.e. trityl, or like protecting group. Guidance for selecting appropriate amino and sulfhydryl protecting groups and $N^\alpha$ protecting groups for selective deprotection may be found in Greene and Wuts, Protecting Groups in Organic Chemistry, $3^{rd}$ Edition (John Wiley & Sons, New York, 1999). Exemplary $R_8$ protecting groups include t-butylcarbamate (Boc), 9-fluorenylmethylcarbamate (Fmoc), 4-nitrophenyl-ethylsulfonyl-ethyloxycarbonyl (NSC), 2,2,2-trichloroethyl-carbamate (Troc), bromobenzylcarbamate (BrZ), chlorobenzylcarbamate (CIZ), 2-(4-biphenylyl)-isopropoxycarbonyl (Bpoc) [Sieber et al., Helv. Chim. Acta, 57:2617-2621 (1968)], α,α-dimethyl-3,5-dimethyloxybenzyloxycarbonyl (Ddz) [Birr et al., Justus Liebigs Ann Chem., 763:162-172 (1972)] and the like. Preferably, $R_8$ protecting groups are Boc, Fmoc and Bpoc. Further exemplary $R_7$ protecting groups include benzyl, 4-methylbenzyl, 4-methoxybenzyl, trityl, acetamidomethyl, trimethylacetamidomethyl, xanthyl, and the like.

Scheme 2 for synthesizing heterocyclic protected oligopeptide thioesters of the invention is shown in FIG. 4. This scheme roughly follows the procedure disclosed by Botti et al (cited above). Bromoacetylated oligopeptide thioester (400) is reacted with S-protected ethylamine or S-protected aminothiophenyl (402), or like group, to give oligopeptide thioester (404) with auxiliary group (406), after which the sulfhydryl protecting group, e.g. triphenylmethyl (trityl), is removed (408) with mild acid, e.g. TFA in the presence of a trityl scavenger, such as TIS. The α-amine of oligopeptide thioester (410) and the free sulfhydryl of the auxiliary group are reacted (412) with carbonyl (414) to form heterocyclic protected oligopeptide thioester (416). Preferably, carbonyl (414) is formaldehyde, acetaldehyde, acetone, or the like. More preferably, $R_1=R_2$ so that chiral forms are not produced that increase the difficulty of purification. On the other hand, in some embodiments, it may be desirable to employ either or both $R_1$ and $R_2$ as an affinity or chromotography purification aid. For example, $R_1$ or $R_2$ may be biotin, digoxigenin, or like affinity group, connected to a linking moiety, e.g. biotin —$(CH_2)_n$—; or $R_1$ or $R_2$ may be a hydrophobic or hydrophilic group designed to modify chromatographic retention time to aid in purification. Heterocyclic protected oligopeptide thioester (416) is deprotected and cleaved from the resin (418), e.g. by HF treatment, to give final product (420).

In scheme 3 of FIG. 5, the heterocyclic protecting group is added to the oligopeptide thioester by coupling a derivatized amino acid already having the group in place. Oligopeptide thioester (500) having a free N-terminal amine is reacted with derivatized amino acid (502) in a conventional solid phase peptide synthesis reaction to give product (504), after which it is deprotected and cleaved (506) from the synthesis column to give final product (508). Derivatized amino acid (502) may be prepared by several routes. Preferably, it is prepared by first synthesizing an intermediate having an auxiliary group-substituted $N^\alpha$ in the following nucleophilic substitution reaction:

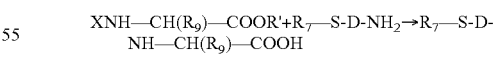

where X is halogen, preferably, bromo, and R' is a conventional protecting group or a solid phase support. Alternatively $R_7$—S-D-NH—C($R_9$)—COOH can be synthesized via reductive amination according to the following scheme:

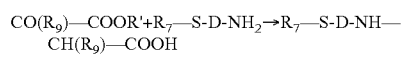

The sulfhydryl of resulting $N^\alpha$-substituted amino acid is deprotected by conventional protocols (e.g. TFA/TIS for trityl-protected sulfhydryl), after which it is reacted with substituted formaldehyde, $CO(R_1)(R_2)$, to give derivatized amino acid (502). Alternatively, the above intermediate may be prepared by the following reaction:

where X is halogen, preferably, bromo, and R' is a conventional protecting group or a solid phase support, or

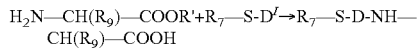

where $D^I$ is a precursor of D (defined above). In one embodiment, $D^I$ contains a carbonyl functionality and the final product $R_7$—S-D-NH—C($R_9$)—COOH is synthesized through reductive amination via reaction with $H_2N$—CH($R_9$)—COOR'. Preferably in this embodiment $D^I$ has the following structure, —$(CH_n)_m$—CO—R", where n=0, 1 or 2, m=1 to 20, and R" is H or a substituted or unsubstituted alkyl or aryl group. More preferably R" is H or a substituted or unsubstituted phenyl or heteroaromatic ring.

Figure 7:
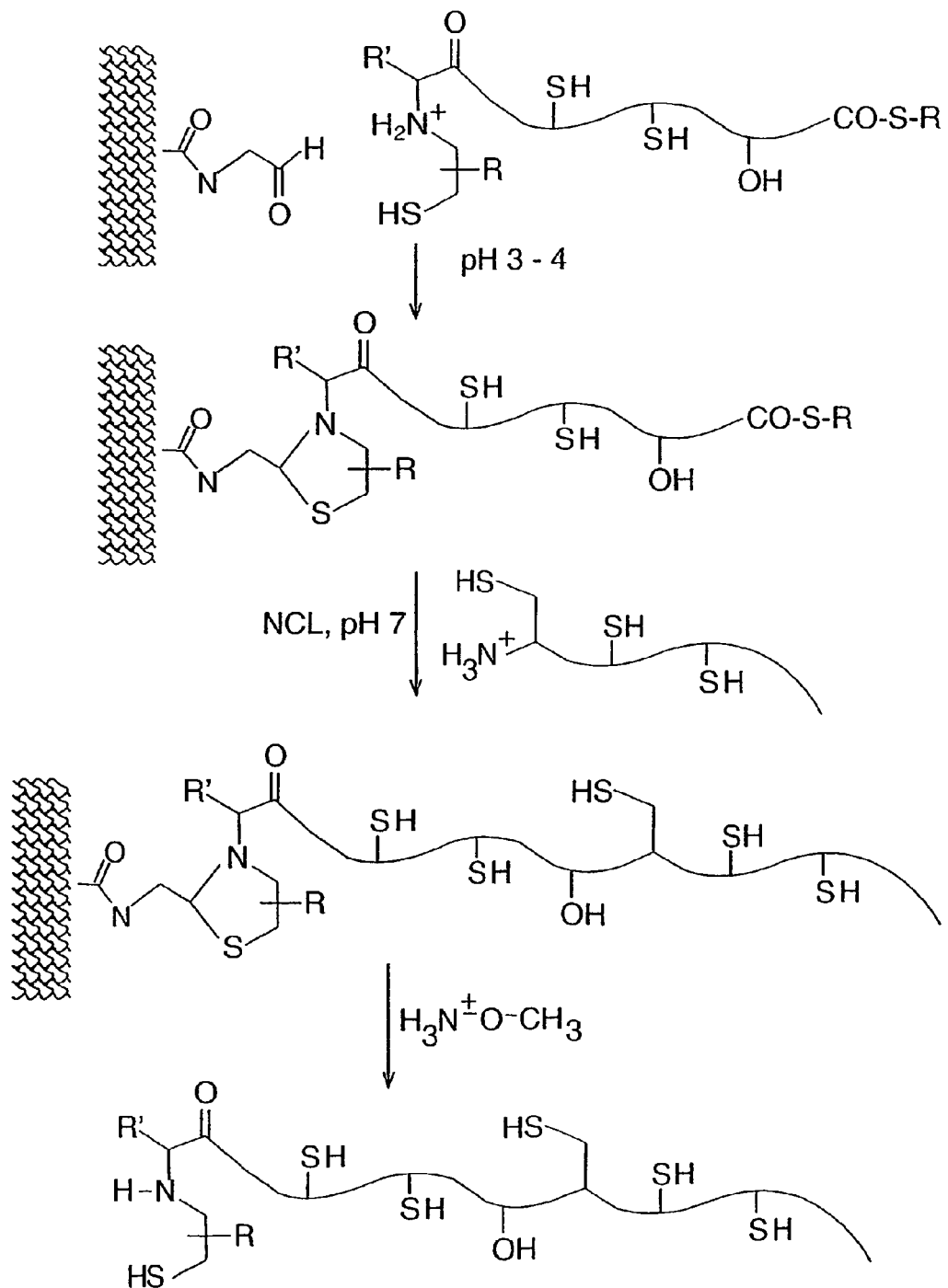
FIG. 7 illustrates concomitant covalent capture and protection of the N-terminal 1,2 amino thiol moiety.

Importantly the protection scheme of the 1,2 or 1,3 N-terminal amino thiol via heterocyclic ring formation can be accomplished in aqueous acidic medium after cleavage on an unprotected oligopeptide Cα-Thioester. (FIG. 7). In such case, if $R_1$ or $R_2$ are part of a solid phase we obtain a concomitant covalent capture and protection of the N-terminal reactive moiety thus providing oligopeptide intermediates that can undergo native chemical ligation to form a polypeptide product in a multi-component synthesis, but that are resistant to self-ligation and concatemerization; providing a heterocyclic protecting group for N-terminal amino acid residues of oligopeptide intermediates of native chemical ligation reactions; providing a method of protecting thioester-modified oligopeptide intermediates from self-ligations or concatemerizations and providing a method for native chemical ligation of successive oligopeptide intermediates via chemical ligation on solid support Preferably, heterocyclic-protected oligopeptide thioester intermediates are used in native chemical ligation under conditions as described by Hackeng et al (1999), or like conditions. Briefly, 0.1 M phosphate buffer (pH 8.5) containing 6 M guanidine, 2% (vol/vol) benzylmercaptan, and 2% (vol/vol) thiophenol is added to dry peptides to be ligated, to give a final peptide concentration of 1-3 mM at about pH 7, lowered because of the addition of thiols and TFA from the lyophilized peptide. Preferably, the ligation reaction is performed in a heating chamber at 37° C. under continuous stirring and is periodically vortexed to equilibrate the thiol additives. The reaction may be monitored for degree of completion by MALDI-MS or HPLC and electrospray ionization MS.

After a native chemical ligation reaction is completed or stopped, the N-terminal heterocyclic ring of the product is opened by treatment with a deprotecting agent that is nucleophilic under acidic conditions, Such agents include certain O-alkylhydroxylamines, hydrazines, and like reagents. More preferably, the N-terminal heterocyclic ring of the product is opened by treatment with O-methylhydroxylamine (0.5 M) at pH 3.5-4.5 for 2 hours at 37° C., after which a 10-fold excess of Tris-(2-carboxyethyl)-phosphine (TCEP) is added to the reaction mixture to completely reduce any oxidizing reaction constituents prior to purification of the product, preferably by conventional preparative HPLC. Preferably, fractions containing the ligation product are identified by electrospray MS, are pooled, and lyophilized. Other reducing agents that can be used in place of Tris-(2-carboxyethyl)-phosphine include β-mercaptoethanolamine, dithiotreitol, and die like.

Deprotecting the heterocycle of the final oligopeptide thioester product is an important feature of the invention and may be accomplished with a variety of agents that are nucleophilic under acidic conditions, as mentioned above. When the heterocyclic protecting group is a thiazolidine, opening the ring under acidic conditions depends on its C2 substituents (Wohr et al, 3. Am. Chem. Soc., 118: 9218 (1994)). The following compounds may be used as thiazolidine deprotecting agents: O-methylhydroxylamine and other hydroxylamine derivatives. Hydrazine or any of its derivatives, as well as thiosemicarbazides, which are nucleophilic under acidic conditions, may also be used, but this family of reagents is more toxic than the former one and the condensation product (hydrazone, thiosemicarbazone, respectively) is less stable than the oxime. Preferably, Tris-(2-carboxyethyl)phosphine (TCEP), or like reducing agent, is used in the deprotection reaction to rapidly and stochiometrically reduces most peptides and sulfhydryls even under acidic conditions (Burns et al., J. Org. Chem., 56:2648-2650, 1991). Preferably, O-methoxyhydroxylamine is used as the thiazolidine deprotecting agent O-methoxyhydroxylamine reacts with the masked aldehyde function in the thiazolidine ring to form an oxime, as shown below.

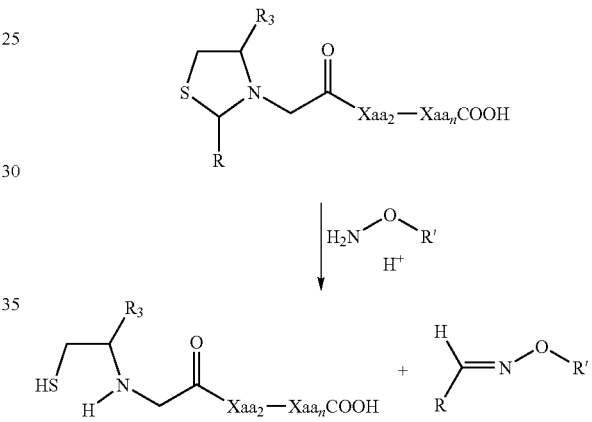

Auxiliary groups may be removed after each ligation step, or they may be removed all at the same time after the polypeptide final product is completely synthesized. Depending on the structure of the linking moiety "D" a variety of removal procedures are available. In the preferred form of D that donates electrons to the $N^\alpha$ of the adjacent amino acid, removal of the auxiliary group may be readily effected by acidic conditions, such as used in conventional peptide synthesis for side chain deprotection. Exemplary, acids for such cleavage include HF, TFA, trifluoromethanesulfonic acid (TFMSA), and the like In some embodiments, conventional scavenging agents, e.g. 5% p-cresol, or the like, may be used to bind or react with aryl, thiol, or other reactive moieties, and to prevent undesired secondary reactions with amino acid side chains.

After the synthesis is completed and the final product purified, the final polypeptide product may be refolded by conventional techniques, e.g. Creighton, Meth. Enzymol., 107: 305-329 (1984); White, Meth. Enzymol., 11: 481484 (1967); Wetlaufer, Meth. Enzymol, 107: 301-304 (1984); Misawa et al, Biopolymers, 51: 297-307 (1999); Anfinsen, Science, 181: 223-230 (1973); and the like. Preferably, a final product is refolded by air oxidation by the following, or like: The reduced lyophilized product is dissolved (at about 0.1 mg/mL) in 1 M guanidine hydrochloride (or like chaotropic agent) with 100 mM Tris, 10 mM methionine, at pH 8.6. After gentle overnight stirring, the re-folded product is isolated by reverse phase HPLC with conventional protocols.

EXAMPLE 1

Synthesis of 1,3-thiazolidine-protected oligopeptide thioester

Figure 6:
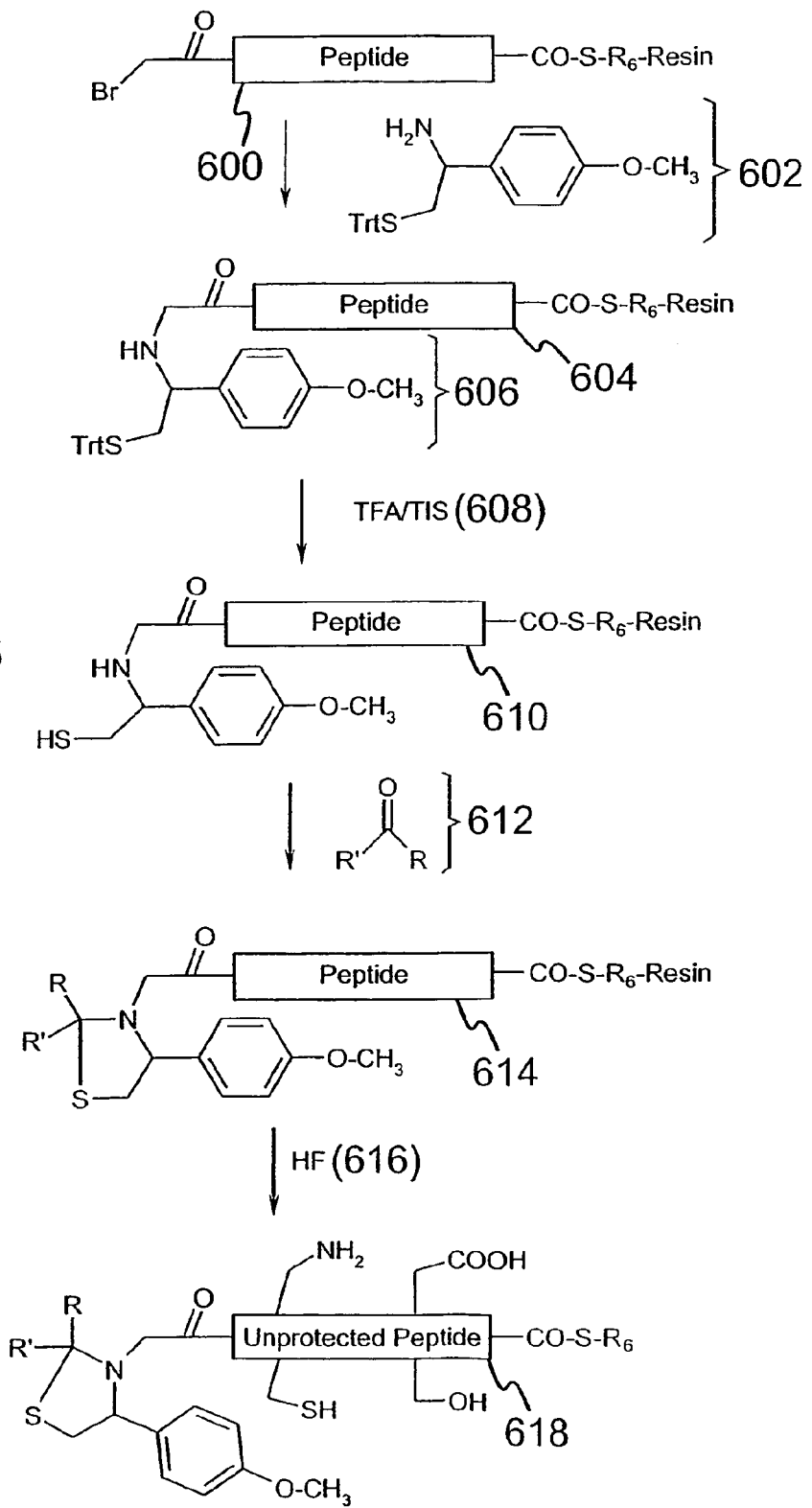
FIG. 6 illustrates the use of scheme 2 for synthesizing a 4-substituted 1,3-thiazolidine-protected oligopeptide thioester.

In this example, an N-terminal 4-substituted 1,3-thiazolidine-protected oligopeptide thioester having amino acid sequence GAVVFVTRKNRQVSANPEKKAVREYIN-SLELL (SEQ ID NO: 2) was synthesized in accordance with scheme 2 outlined above, and illustrated in FIG. 6.

Bromoacetylated oligopeptide thioester (600) was prepared as follows: AVVFVTRKNRQVSANPEKKAVREY-INSLELL (SEQ ID NO: 3) was synthesized using conventional peptide chemistry as described above in a 0.1 mmole scale, after which its α-amine was deprotected by treatment with TFA followed by neutralization with 10% diisopropylethylaniine (DIEA) (Aldrich). 4 mmole BrCH$_2$COOH (MW=133.91(555 mg)) was combined with 2 mmole diisopropylcarbodiimide (DIC) in 3 mL dimethylformamide (DMF) (6.65 M, or 310 µL) and incubated at room temperature for 15-20 minutes, after which the solution was added to the deprotected oligopeptide on the resin. The deprotected oligopeptide and resin were incubated at room temperature in this solution for at least an hour. After measuring the completeness of the bromoacetylation by a conventional ninhydrin test, the bromoacetylated oligopeptide and resin were washed with DMF and then with DMSO. Protected auxiliary group, 1-(4-methoxyphenyl)-2-(tritylthio)-ethylamine (602) (1.5 equivalent or 0.15 mmole), prepared as described in Botti et al (cited above), was dissolved in 2 µL DMSO and 3 equivalents of DIEA (0.3 mmole) to give 51 µL of solution, which was then added to the bromoacetylated oligopeptide and incubated overnight to give N$^α$-(1-4-methoxyphenyl)-2-(tritylthio)-ethyl)-GAVVFVTRKNRQVSANPE-KKAVREYINSLELL-(CO)—S-resin (SEQ ID NO:6) (604). The trityl-protected sulfhydryl of the auxiliary group was then deprotected (608) by 2× treatment with TFA/TIS/H2O (95/2.5/2.5) to give (610), after which the oligopeptide and the deprotected auxiliary group were washed with DMF. The free sulfhydryl of the auxiliary group was cyclized with the N$^α$ of the terminal glycine by treatment with formaldehyde (612 where R$_1$=R$_2$=H) (in 100-fold excess of the auxiliary group on resin, i.e. 765 µL of 36% solution in H$_2$O combined with 3 mL DMF, or about 10 mmole) and 500 µL acetic acid to give resin-bound 1,3-thiazolidine-protected oligopeptide thioester (614). After incubation for 4-5 hours, the resin was washed and dried for full deprotection by HF. After drying, the heterocyclic-protected oligopeptide thioester (614) was deprotected and cleaved (616) from the resin using HF to give final product (618).

EXAMPLE 2

Synthesis of N$^α$-(5-methoxyphenyl-1,3-thiazolidine)-substituted glycine

In this example, heterocylic-protected glycine is synthesized by first forming an N$^α$-(auxiliary group)-substituted glycine, followed by deprotection and then cyclization by reaction with formalehyde. Triphenylmethyl mercaptan (Aldrich), 4 mmol, and 4'-methoxy-2-bromoacetophenone (Aldrich), 4 mmol, are dissolved in 2 mL DMF, after which 4 mmol DIEA is added. The mixture is stirred at room temperature for 1 hour, after which it is poured in diluted HCl, extracted with ethylacetate, and dried over sodium sulfate. The resulting oil is dissolved in ethylacetate and precipitated by addition of petroleum ether, which after evaporation gives a white solid, 4'-methoxy-2-(triphenylmethylthio)-acetophenone. This compound, 1.44 mmol, and aminoxyacetic acid, 4.3 mmol, are dissolved in 20 mL of trimethylorthoformate (TMOF), after which 0.047 mL of methanesulfonic acid is added as a catalyst. After incubation at room temperature for 48 hours, the solvent is evaporated and the residue taken up in ethylaceetate, washed with 1M monohydrogenpotassium sulfate and dried over sodium sulfate, after which the crude product is purified with silica gel chromatography and an oxime complex is isolated. 0.556 mmol of the oxime complex is dissolved in 2 mL of tetrahydrofuran (THF) and 1.67 mL of 1 M BH3/THF complex is added. After 24 hours, 3 mL of water and 1.5 mL of 10 N sodium hydroxide is added and the mixture is refluxed for 1 hour, after which the mixture is extracted with ethylacetate (4×) and dried over sodium sulfate. The final product of 1-amino-1-(4-methoxyphenyl)-2-(triphenylmethylthio)-ethane, is purified using silica gel chromatography. The 1-amino-1-(4-methoxyphenyl)-2-(triphenylmethylthio)-ethane is then reacted with BrNα-glycine in the presence of a base to give the N$^α$-(auxiliary group)-substituted glycine, preferably attached to a solid phase support. After deprotecting the sulfhydryl of this compound by treatment with TFA/TIS as described above, the cyclization reaction is carried out by treatment with formaldehyde. The final product is cleaved from the solid phase support by conventional means.

Alternatively, Boc-protected N$^α$-1-(4'-methoxyphenyl)-2-(triphenylmethylthio)-ethyl glycine may be prepared as follows. 4'-methoxy-2-(triphenylmethylthio) acetophenone, 2 mmol, and glycine ethyl ester HCl salt, 2 mmol, are suspended in 15 mL of dichloromethane, after which 1 mL of titanium tetrachloride (1 M solution) and DIEA, 6 mmol, is added, the latter slowly under nitrogen. After incubation at room temperature for 48 hours, sodium cyanoborohydride, 6 mmol, in 2.5 mL of anhydrous methanol is added to give a final product of N$^α$-1-(4'-methoxyphenyl)-2-(triphenylmethylthio)-ethyl Boc-glycine ethylester. After dissolving 1 mmol of this product in 2 mL of THF, 2 mmol of LiOH hydrate is added. After overnight stirring to completely hydrolyze the ester, THF is removed by vacuum and the remaining material is mixed with 2 mL DMF, 5 mmol of dibutyl dicarbonate, and 3 mmol of DIEA. After overnight reaction, a dilute HCl water solution is added and the final product is extracted three times with ethyl acetate.

EXAMPLE 3

Ligation of N$^α$-(1-methyl-5-methoxyphenyl-1,3-thiazolidine)-Protected Oligopeptide Thioester In this example, an N$^α$-(1-methyl-5-methoxyphenyl-1,3-thiazolidine)-protected oligopeptide thioester (fragment 2) was ligated in solution to oligopeptide (fragment 1) having an N-terminal cysteine. The masses of the reactants were determined by electrospray mass spectrometry (model Esquire, Brücker Bremen, Germany) to be 958 for fragment 1 and 4008 for fragment 2.

| Fragment | SEQ ID NO: | Sequence of Oligopeptide Reactant |
| --- | --- | --- |
| 1 | 1 | CYAKYAKL-COOH |
| 2 | 7 | thiazolidine-GAVVFVTRKNRQVSANPEKKAVREYINSLELL-thioester |

Thioester formation. Fragment 2 was synthesized on a thioester generating resin. For this purpose S-acetylthioglycolic acid pentafluorophenylester was coupled to a Leu-PAM resin under conditions essentially as described by Hackeng et al (cited above). The resulting resin was used as a starting resin for peptide chain elongation on a 0.2 mmol scale after removal of the acetyl protecting group with a 30 min treatment with 2M mercaptoethanol, 2M piperidine in DMF. The thioester was formed with Boc-Leu-OH for synthesis of fragment 2 using the standard in situ neutralization coupling protocol for 1 hour, Schnölzer et al (cited above), with a 4-fold molar excess of amino acid over the sulfhydryl group.

Peptide synthesis. Solid-phase synthesis of Fragments 1 and 2 were performed on a custom-modified 433A peptide synthesizer from Applied Biosystems, using in situ neutralization/2-(1H-benzotriazol-1-yl)-1,1,1,3,3-tetramethyluronium hexafluoro-phosphate (HBTU) activation protocols for stepwise Boc chemistry chain elongation, as described by Schnolzer et al, Int. J. Peptide Protein Res., 40: 180-193 (1992). Each synthetic cycle consisted of $N^\alpha$-Boc-removal by a 1 to 2 min treatment with neat TFA, a 1-min DMF flow wash, a 10-min coupling time with 2.0 mmol of preactivated Boc-amino acid in the presence of excess DIEA and a second DMF flow wash. N$\alpha$-Boc-amino acids (2 mmol) were preactivated for 3 min with 1.8 mmol HBTU (0.5M in DMF) in the presence of excess DIEA (6 mmol). After coupling of Gln residues, a dichloromethane flow wash was used before and after deprotection using TFA, to prevent possible high temperature (TFA/DMF)-catalyzed pyrrolidone carboxylic acid formation. Where applicable, side-chain protected amino acids were Boc-Arg(p-toluenesulfonyl)-OH, Boc-Asn(xanthyl)-OH, Boc-Asp(O-cyclohexyl)-OH, Boc-Cys(4-methylbenzyl)-OH, Boc-Glu(O-cyclohexyl)-OH, Boc-His(dinitrophenylbenzyl)-OH, Boc-Lys(2-Cl—Z)—OH, Boc-Ser(benzyl)-OH, Boc-Thr(benzyl)-OH, Boc-Trp(formyl)-OH and Boc-Tyr(2-Br—Z)—OH (Orpegen Pharma, Heidelberg, Germany). Other amino acids were used without side chain protection.

The N-terminal $N^\alpha$-(1-methyl-5ethoxyphenyl-1,3-thiazolidine)-protected glycine was formed on Fragment 2 as described in Example 1, with the exception that free sulfhydryl of the auxiliary group was cyclized with the $N^\alpha$ of the terminal glycine by treatment with methyl-substituted formaldehyde (i.e., $R_1$=H and $R_2$=$CH_3$).

After chain assembly was completed, the peptides were deprotected and cleaved from the resin by treatment with anhydrous hydrogen fluoride for 1 hr at 0° C. with 5% presol as a scavenger. After cleavage, both peptides were precipitated with ice-cold diethylether, dissolved in aqueous acetonitrile containing 0.1% TFA and lyophilized. The peptides were purified by RP-HPLC with a C18 column from Waters by using linear gradients of buffer B (acetonitile/0.1% trifluoroacetic acid) in buffer A (H0/0.1% trifluoroacetic acid) and UV detection at 214 nm. Collected fractions were analyzed by electrospray mass spectrometry (ESMS) using an Esquire instrument (Brücker, Bremen, Germany) and by analytical HPLC. Fractions containing the right product were pooled and freeze-dried.

Native chemical ligation. Ligation of unprotected fragments was performed as follows: the dry peptides were dissolved in equimolar amounts (1.0 mg fragment 1 and 4.4 mg fragment 2) in 6M guanidine hydrochloride (GuHCl), 0.2M phosphate, pH 7.5 in order to get a final peptide concentration of 1-5 mM at a pH around 7, and 2% thiophenol was added. The reaction was carried out overnight and was monitored by HPLC and electrospray mass spectrometry. The ligation product was subsequently treated to hydrolyze any remaining thioester and to remove protecting groups still present. For this purpose, 20% 2-mercaptoethanol was added and the pH shifted to 9.0 by addition of hydrazine and the solution incubated for 1 h at 37° C. To open the thiazolidine ring, the reaction mixture was then acidified to pH 3.5 with 6M HCl and 2M O-methylhydroxylamine in 6M guanidinehydrochloride, pH3.5 added to get a final 0.5M concentration. A 2 h incubation at 37° C. is required for complete opening of the N-terminal thiazolidine ring. A 10-fold excess of Tris(2-carboxyethyl)phosphine over the fragment was added and the material purified by preparative HPLC after 15 min incubation. Fractions containing the polypeptide chain were identified by ESMS, pooled and lyophilized.

Figure 8B:
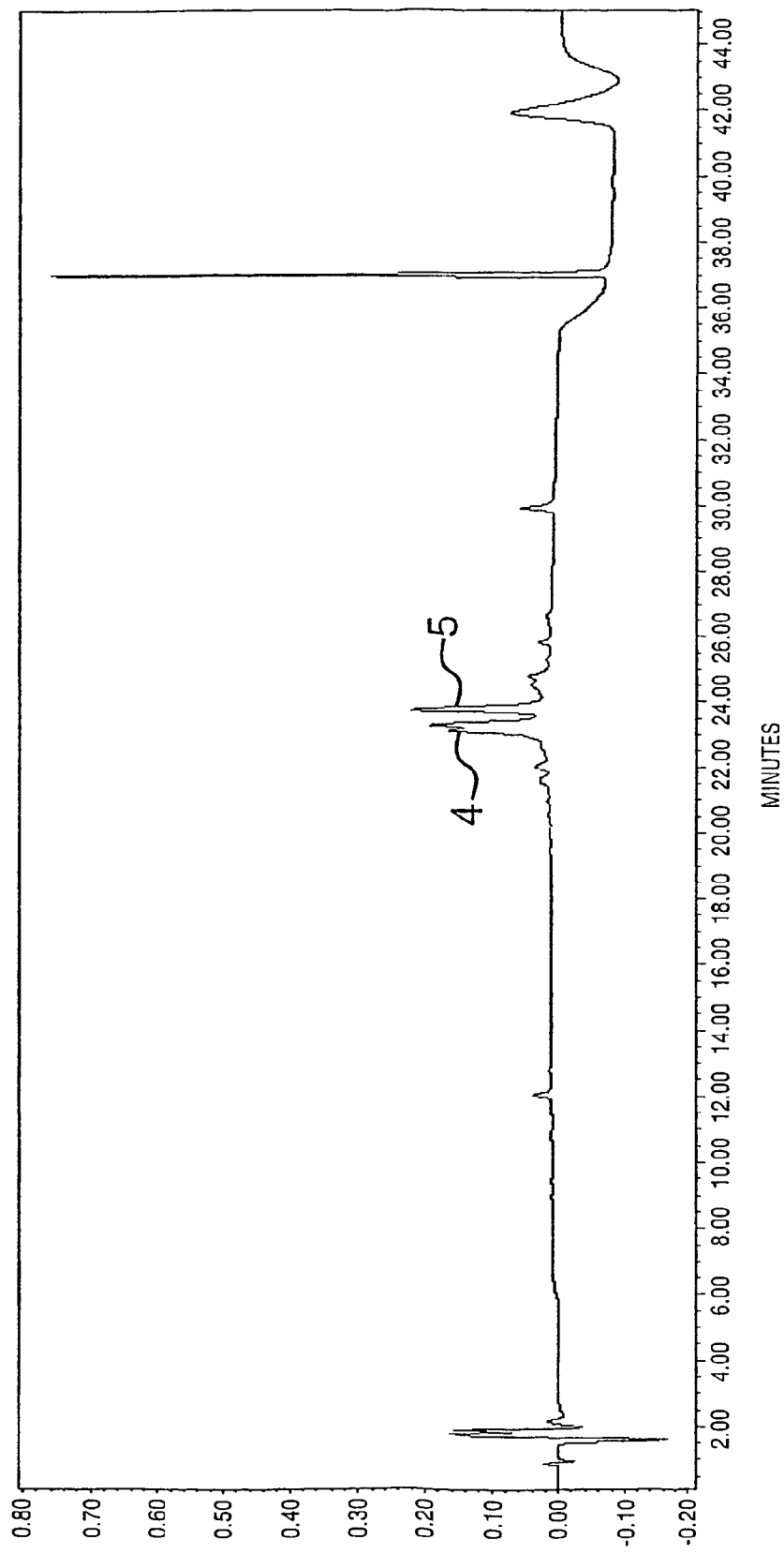
FIG. 8B is a chromatogram of a ligation product after 12 hours (T=12 h).
Figure 8C:
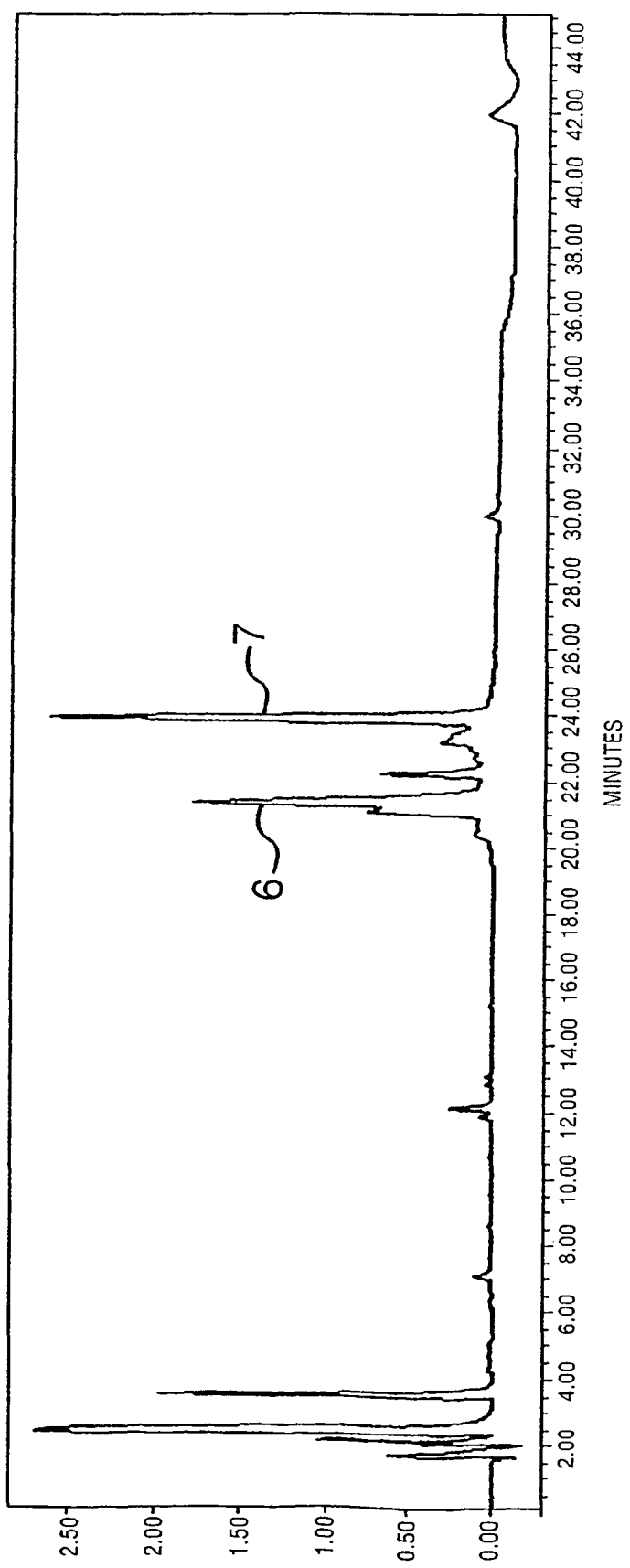
FIG. 8C is a chromatogram of a ligation product after deprotection (T=3 h after addition of NOC).
Figure 9:
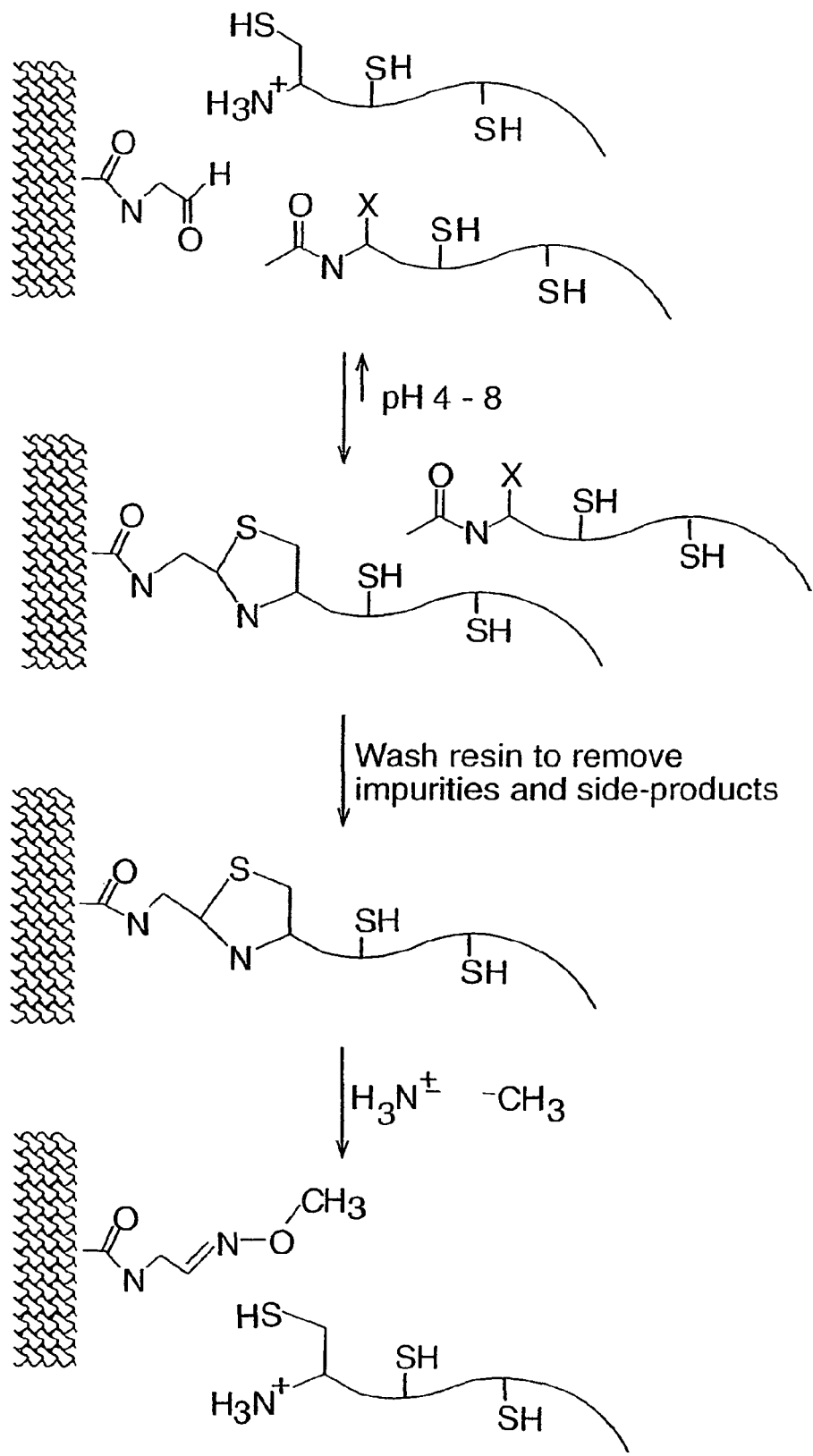
FIG. 9 Scheme of covalent capture purification procedures.
Figure 10:
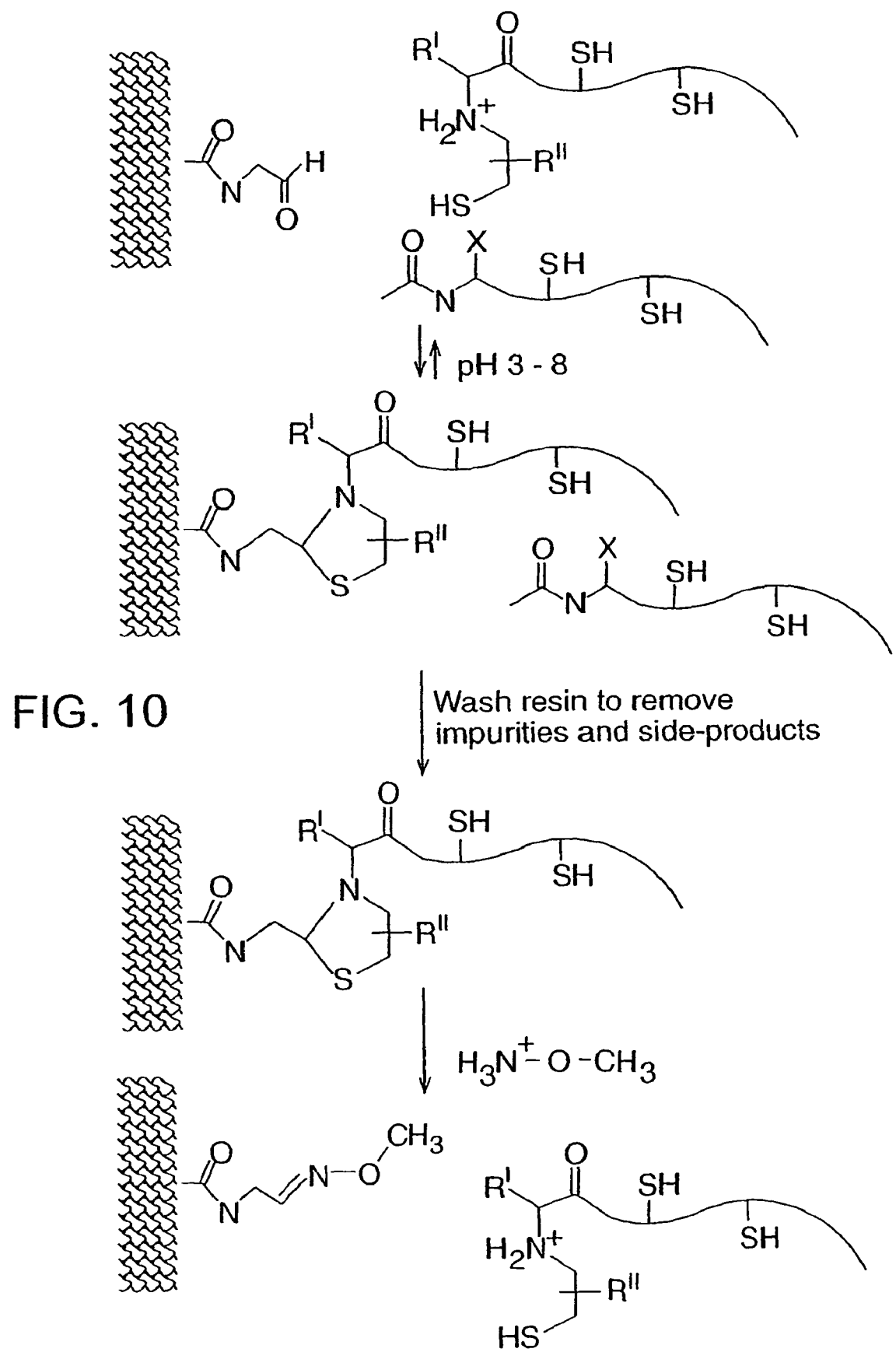
FIG. 10 Scheme of covalent capture purification procedures applied to Native Chemical Ligation at non-cysteine site.
Figure 11A:
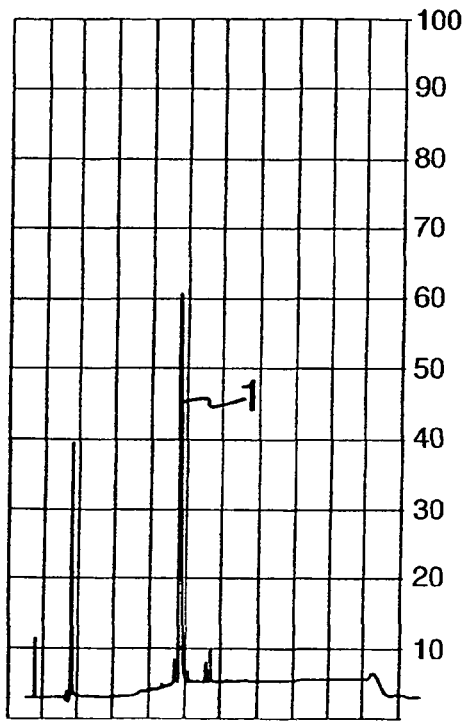
FIG. 11 illustrates the capture step on solid support. 11A: ELC peptide covalent capture T=0, ALIFS 1.0 220 nm 2 µl of reaction+30 µl A inj=20 µl. 11B: T=1 h30. 11C: T=3 h30. 11D: T=24 h.
Figure 11B:
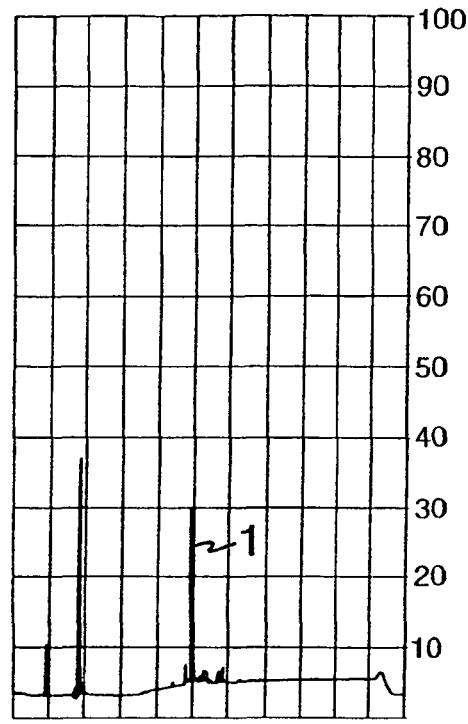
Figure 11C:
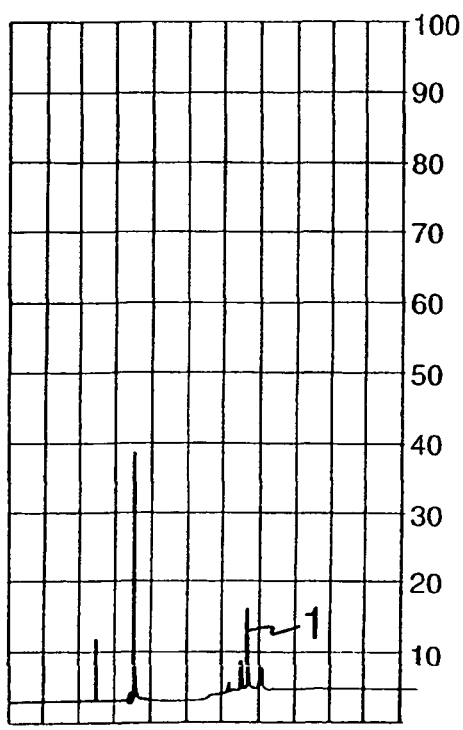
Figure 11D:
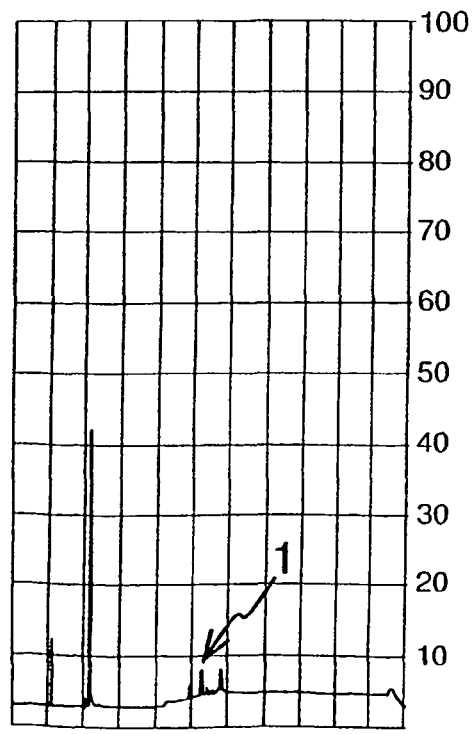
Figure 12A:
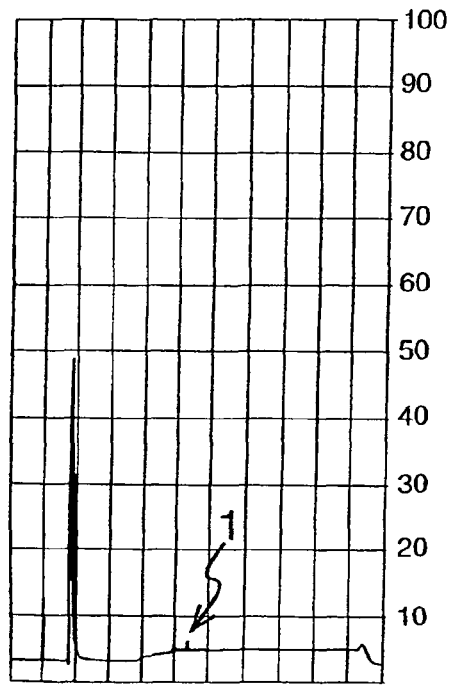
FIG. 12 illustrates the elution step from the solid support. 12A: ELC peptide release O-carboxymethyl hydroxylamine.HCl T=0. 12B: T=1 h30. 12C: T=3 h30. 12D: T=24 h.
Figure 12B:
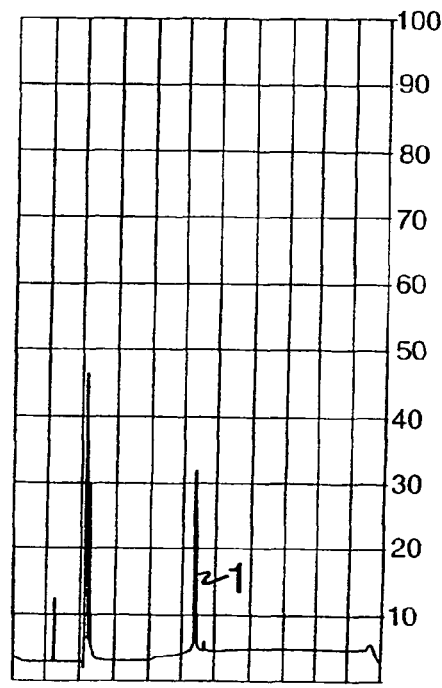
Figure 12C:
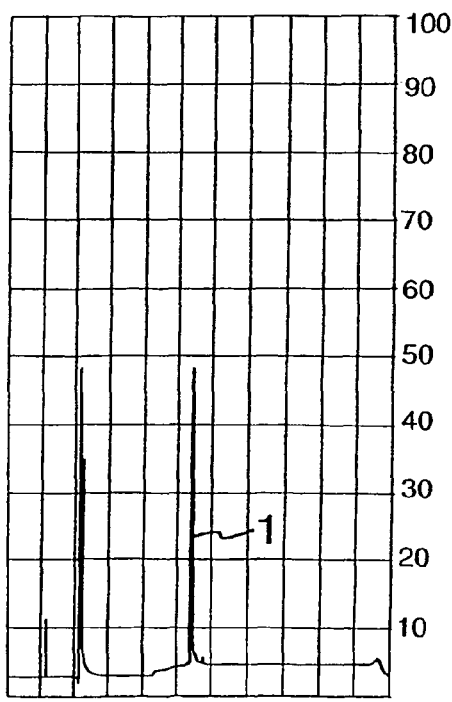
Figure 12D:
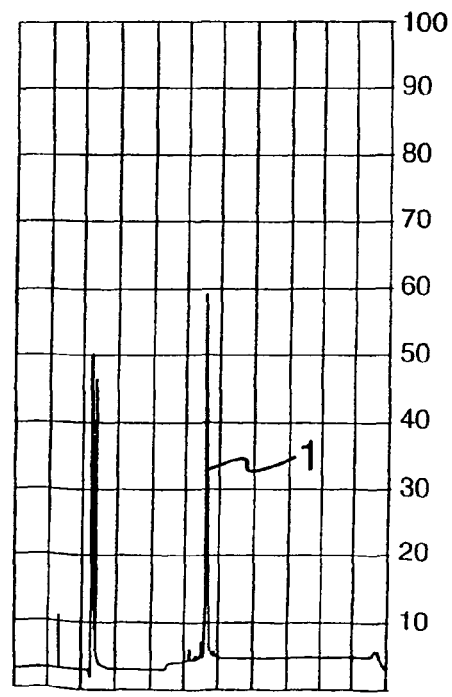
Figure 13A:
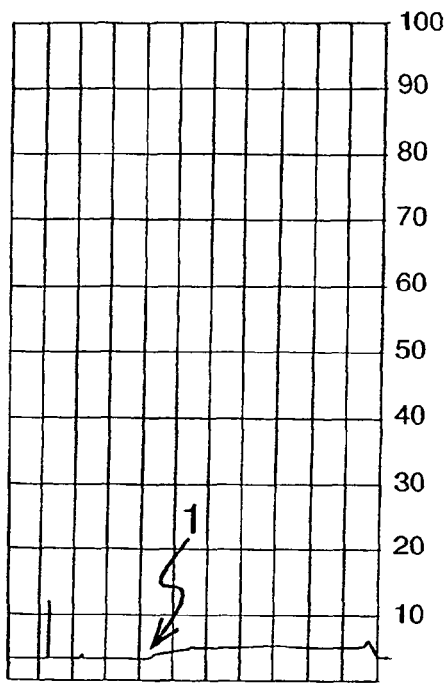
FIG. 13 illustrates the elution step from the solid support. 13A: ELC peptide release O-methyl hydroxylamine.HCl T=0. 13B: T=1 h30. 13C: T=3 h30. 13D: T=24 h.
Figure 13B:
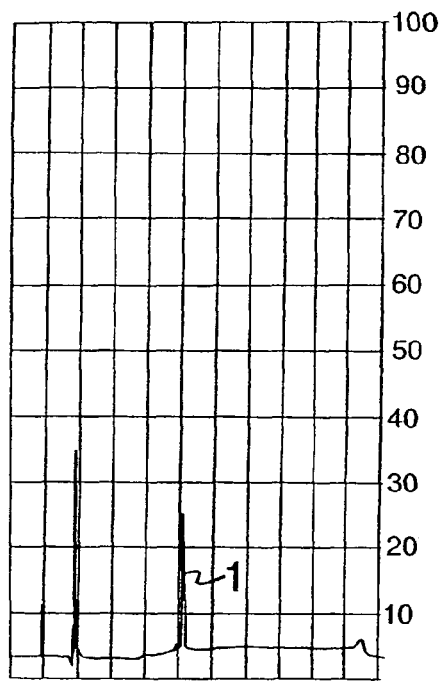
Figure 13C:
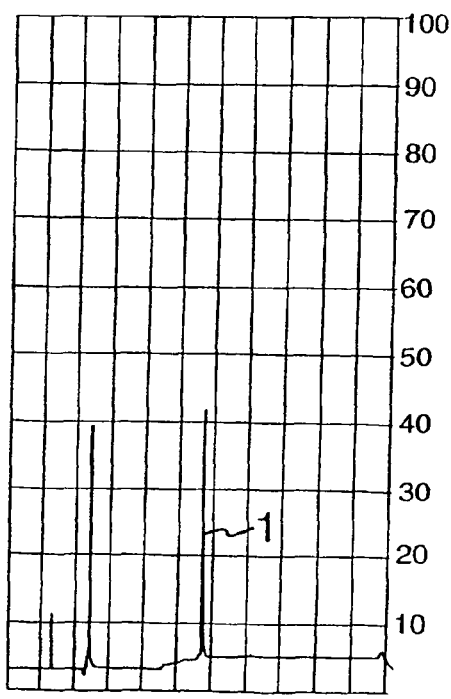
Figure 13D:
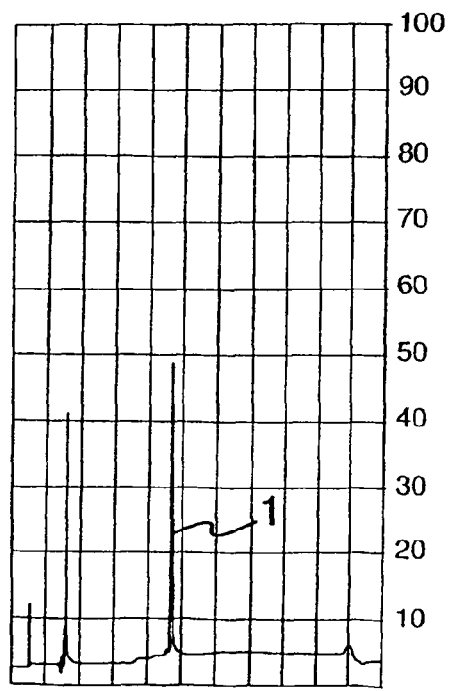

Results of the ligation and ring opening reactions are shown in the chromatograms of FIGS. 8A to 8C. Peak 1 of FIG. 8A is Fragment 1 and peak 2 is a dimmer of Fragment 1 formed by a disulfide bridge between the terminal cysteines. Peak 3 is the heterocyclic-protected Fragment 2. The multiple peaks of peak 3 results from the presence of chiral centers in the heterocyclic protecting group. Peak 4 of FIG. 8B is the ligation product of Fragments 1 and 2. Peak 5 is the thiophenyl catalyst Peak 6 of FIG. 8C is the deprotected ligation product, i.e. with the hetercyclic protecting group opened Peak 7 of FIG. 8C is again the thiophenyl catalyst.

EXAMPLE 4

Application of the Covalent Capture Strategy to the N-Terminal Modified Amino Acid Peptide Fragment N-Terminal AA (Aux)-Peptide) Suitable for the Extended Chemical Ligation (Native Chemical Ligation at Non Cysteine Residues)

Capture Step

A model peptide of sequence Gly (Aux) YAKYAKAL (SEQ ID NO: 4) with Aux=$N^\alpha$-(1-(4-methoxyphenyl)-2-mercaptoethyl is dissolved in 50% acetate buffer 0.1N 50% MeCN with a final pH of 4.4 at room temperature and then added to a CHO functionalised PEGA resin (FIG. 11) as described in literature: Villain et al, Chem Biol. 2001 July; 8(7):673-9; Rose et al, International Patent Application PCT/GB01/01803 (WO01/18367). Panels A through D show the capture of the peptide by the functionalised support over time. Peak 1 in the chromatogram of panel A shows the free peptide concentration at the start of the capture reaction. Peak 1 of panels B and C show the concentration of free peptide at times 1 h30 m and 3 h30 m, respectively. The chromatogram of panel D shows that the peak corresponding to the model peptide has essentially disappeared.

Elution Step

Figure 14:
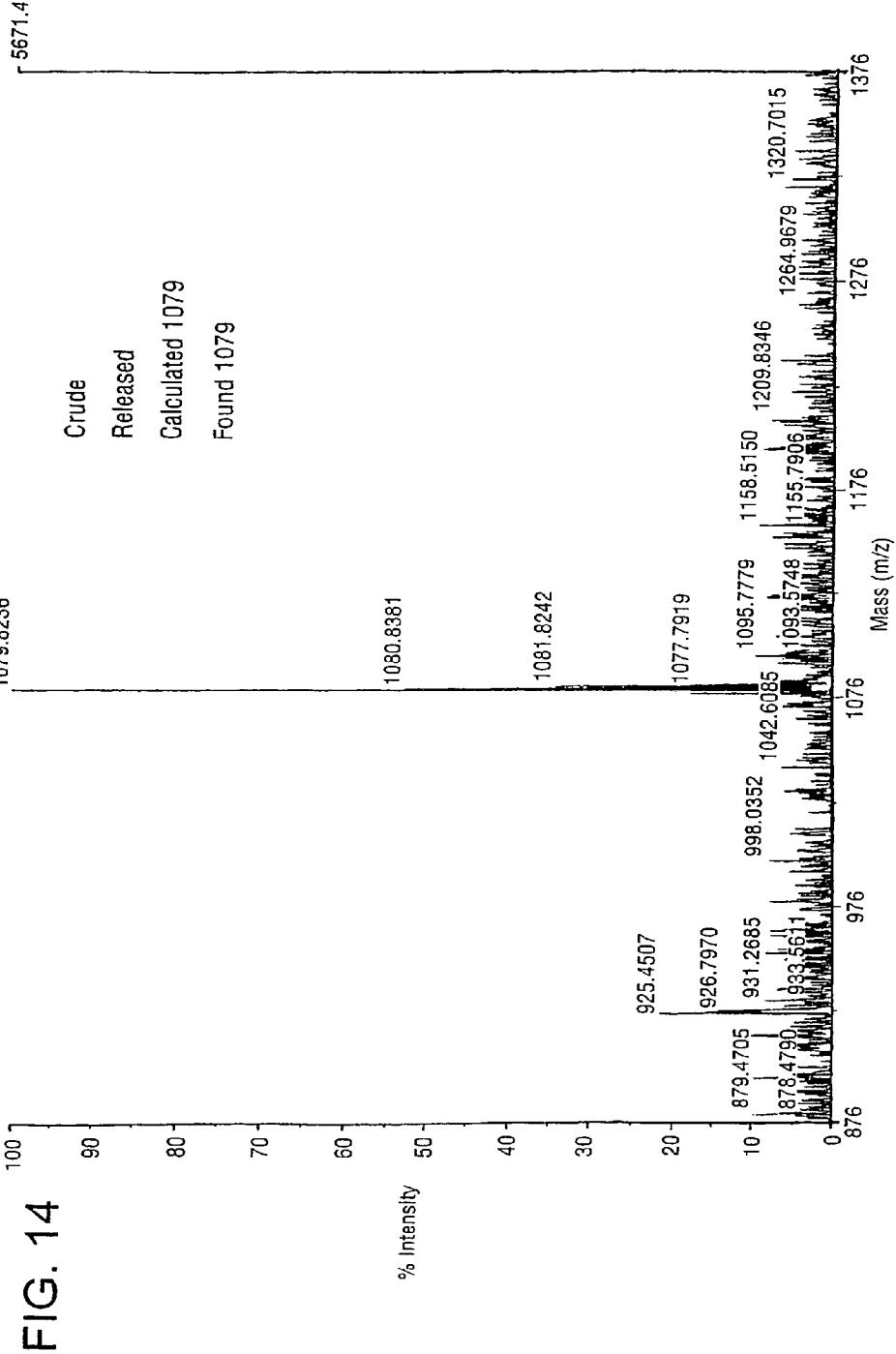
FIG. 14 is a mass spectrogram of the eluted material of FIGS. 12 and 13.

The elution of the peptide is then accomplished as reported in literature:

Acetate buffer 0.1N 10 mM Tcep, with 0.5M O-Carboxymethylhydroxylamine (FIG. 12) or 0.5M O-Methylhydroxylamine (FIG. 13). In FIG. 12, the chromatogram of the eluant (panel A) at 0 h0 m shows the absence of a peak (1) corresponding to the model peptide. That is, no released material is present in solution at time zero. Peak 1 shown in panels B, C, and D, respectively, shows progressive increases in the concentration of the released model peptide at times 1 h30 m, 3 h30 m, and 24 h0 m, respectively. In FIG. 13, essentially the same pattern of release is demonstrated by the absence of a peak (1) in panel A and the progressive increase of model peptide concentrations in panels B through D. FIG. 14 is a mass spectrogram of the eluted material showing that the mass corresponding to the primary peak (1) is equivalent to the computed weight of the model peptide.

The descriptions of the foregoing embodiments of the invention have been presented for purpose of illustration and description. They are not intended to be exhaustive or to limit the invention to the precise forms disclosed, and obviously many modifications and variations are possible in light of the above teaching. The embodiments were chosen and described in order to best explain the principles of the invention to thereby enable others skilled in the art to best utilize the invention in various embodiments and with various modifications as are suited to the particular use contemplated. It is intended that the scope of the invention be defined by the claims appended hereto.

---

The invention claimed is:
1. A composition of matter comprising an N-terminal heterocyclic-protected oligopeptide thioester defined by the following formula:

FORMULA II

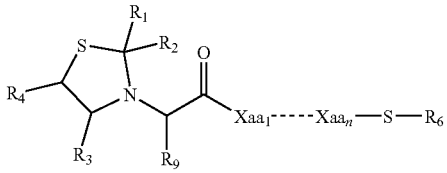

wherein:
  each of $Xaa_1$ to $Xaa_n$, is independently a protected or unprotected amino acid;
  n is an integer from 2 to 120;
  $R_1$ is hydrogen;
  $R_2$ is hydrogen, unsubstituted alkyl having from 1 to 3 carbon atoms or an electron withdrawing-substituted alkyl having from 1 to 3 carbon atoms, said electron withdrawing substituent-selected from the group consisting of: halo, cyano, nitro-substituted alkyl having from 1 to 3 carbon atoms, carbonyl, carboxy, carboxyester, carboxyamide, amidocarboxy, amidocarbonyl, sulfoxy, sulfone and quarternary ammonium salts, wherein $R_2$ may optionally be attached to a solid support;
  $R_3$ is hydrogen or an electron donating group having from 1 to 12 carbon atoms and from 0 to 4 heteroatoms selected from the group consisting of nitrogen, oxygen, sulfur, and phosphorus;
  $R_4$ is hydrogen, alkyl having from 1 to 3 carbon atoms, aryl or electron donating-substituted aryl having 6-10 carbon atoms with 0-2 heteroatoms, or electron donating-substituted alkyl having from 1 to 3 carbon atoms;
  $R_6$ is alkyl having from 1 to 6 carbon atoms, alkylaryl having from 6 to 8 carbon atoms, —$CH_2$—$CONH_2$, —$CH_2CH_2CONH_2$, or —$(CH_2)_k$—CO—Xaa, wherein k is an integer equal to 1 or 2 and Xaa is an amino acid; and
  $R_9$ is a side chain of an amino acid selected from the group consisting of alanine, aspartic acid, glutamic acid, phenylalanine, glycine, histidine, lysine, leucine, methionine, asparagine, glutamine, arginine, serine, tryptophan, and tyrosine.

2. The composition of claim 1 wherein:
  $R_3$ is hydrogen, or a group having from 1 to 8 carbon atoms and from 0 to 2 heteroatoms selected from the group consisting of nitrogen, oxygen, and sulfur;
  $R_4$ is hydrogen; and
  $R_9$ is a side chain of an amino acid selected from the group consisting of glycine, alanine, and histidine.

3. The composition of matter according to claim 1, wherein n is an integer from 2 to 70.

4. The composition of claim 3 wherein:
  $R_3$ is hydrogen, phenyl, substituted phenyl, 2-picolyl, 4-picolyl, substituted 2-picolyl, or substituted 4-picolyl;
  $R_4$ is hydrogen; and
  $R_9$ is a side chain of an amino acid selected from the group consisting of glycine, alanine, and histidine.

5. The composition of claim 4 wherein $R_3$ taken alone is hydrogen or methoxy-substituted phenyl.

6. The composition of claim 3 wherein
  $R_2$ is electron withdrawing-substituted alkyl having from 1 to 3 carbon atoms.

7. The composition of claim 3 wherein
  $R_2$ is hydrogen,
  $R_3$ is 4-methoxyphenyl, and
  $R_4$ is hydrogen.

* * * * *